United States Patent
Zimmerman et al.

(10) Patent No.: US 12,318,417 B2
(45) Date of Patent: Jun. 3, 2025

(54) *LACTOBACILLUS* COMPOSITIONS AND METHODS FOR PREVENTION AND TREATMENT OF MICROBIAL INFECTION

(71) Applicant: Church & Dwight Co., Inc., Princeton, NJ (US)

(72) Inventors: Noah Paul Zimmerman, Chapel Hill, NC (US); Amy Wescott, Rubicon, WI (US)

(73) Assignee: Church & Dwight Co., Inc., Princeton, NJ (US)

( * ) Notice: Subject to any disclaimer, the term of this patent is extended or adjusted under 35 U.S.C. 154(b) by 462 days.

(21) Appl. No.: 17/557,939

(22) Filed: Dec. 21, 2021

(65) Prior Publication Data

US 2022/0193157 A1    Jun. 23, 2022

Related U.S. Application Data

(60) Provisional application No. 63/129,941, filed on Dec. 23, 2020.

(51) Int. Cl.
| | | |
|---|---|---|
| *A61K 35/747* | (2015.01) | |
| *A61P 31/04* | (2006.01) | |
| *C12N 1/20* | (2006.01) | |
| *C12R 1/225* | (2006.01) | |

(52) U.S. Cl.
CPC ............ *A61K 35/747* (2013.01); *A61P 31/04* (2018.01); *C12N 1/205* (2021.05); *C12R 2001/225* (2021.05)

(58) Field of Classification Search
None
See application file for complete search history.

(56) References Cited

U.S. PATENT DOCUMENTS

| | | | |
|---|---|---|---|
| 6,479,051 | B1 | 11/2002 | Bruce et al. |
| 9,011,839 | B2 | 4/2015 | Hsieh et al. |
| 10,004,770 | B2 | 6/2018 | Versalovic et al. |
| 2018/0264055 | A1 | 9/2018 | Versalovic et al. |
| 2019/0070229 | A1 | 3/2019 | Choi et al. |

FOREIGN PATENT DOCUMENTS

| | | |
|---|---|---|
| CN | 100574767 | 12/2009 |
| CN | 105087436 | 11/2015 |
| CN | 110373342 A | 10/2019 |
| CN | 107267415 | 2/2020 |
| DE | 102017113263 | 12/2018 |
| EP | 0698347 | 7/2006 |
| WO | 2016026474 | 2/2016 |
| WO | WO-2016026474 A1 * | 2/2016 ........... A61K 35/747 |

OTHER PUBLICATIONS

Gregorio et al. Journal of Applied Microbiology vol. 118, pp. 1034-1047, 2014.*
Damayanti et al. Technology and Life Science pp. 239-246, 2019. (Year: 2019).*
Talarico et al. Antimicrobial Agents and Chemotherapy vol. 32, No. 12, pp. 1854-1858, 1988 (Year: 1988).*
Casas et al. Microbiology Ecology in Health Disease vol. 12, pp. 247-285, 2000 (Year: 2000).*
Extended European Search Report issued Oct. 8, 2024, in corresponding European Application No. 21912051.6.
Eslami, Gita et al., "Inhibitory Effect of Lactobacillus reuteri on Some Pathogenic Bacteria Isolated From Women With Bacterial Vaginosis," Avicenna Journal of Clinical Microbiology and Infection, vol. 1(2), Aug. 30, 2014, pp. 19908-19908.
Shahzadi, Kiran et al., "Lactobacillus reuteri can reduce Gardnerella induced bacterial vaginosis in mice and modulate immune markers," Apr. 17, 2020, 22 pages. Retrieved from the Internet: https://www.researchsquare.com/article/rs-23647/v1.
Mastromarino, Paola et al., "Bacterial vaginosis: a review on clinical trials with probiotics," New Microbiologica, vol. 36(3), Jul. 1, 2013, pp. 229-238.
Castrellon: "Clinical Trial of L. Reuteri in Urinary Tract Infections in Non Pregnant Women," Nov. 29, 2017, 10 pages. Retrieved from the Internet: https://clinicaltrials.gov/study/NCT03019172.
De Gregorio, et al., "Preventive effect of Lactobacillus reuteri CRL 1324 on Group B *Streptococcus* vaginal colonization in an experimental mouse model," Journal of Applied Microbiology, Apr. 2015, vol. 118, No. 4, p. 1034-1047. Abstract; p. 1036, col. 2, para 4. US.
International Search Report for related International Application No. PCT/US2021/064631, dated May 18, 2022.
Casas, et al., "Validation of the Probiotic Concept: Lactobacillus Reuteri confers broad spectrum protection against disease in humans and animals", Microbial Ecology in Health and Disease (2000), vol. 12, Issue 4, pp. 247-285. US.
Darmayanti, et al., "Giving Probiotic for a Better Therapy of Bacterial Vaginosis", ICO-HELICS, the 1st International Conference on Health, Technology and Life Sciences, 2019, pp. 239-246. ID.
Jorgensen, et al., "Probiotic lactobacillus reuteri has antifungal effects on oral *Candida* species in vitro", Journal of oral Mictobiology (2017), vol. 9, p. 1-9. DK.
Spinler, et al., "Human-derived probiotic Lactobacillus reuteri demonstrate antimicrobial activities targeting diverse enteric bacterial pathogens", Anaerobe, vol. 14, Issue 3 (2008), pp. 166-171. US.

* cited by examiner

*Primary Examiner* — Jana A Hines
*Assistant Examiner* — Khatol S Shahnan Shah
(74) *Attorney, Agent, or Firm* — Church & Dwight Co., Inc.

(57) ABSTRACT

The present invention relates to microbial compositions containing *Lactobacillus*, and methods for reducing growth of microbes that cause infection, such as urogenital tract infection and for treating or preventing the same using the compositions thereof.

20 Claims, 10 Drawing Sheets

LACTOBACILLUS COMPOSITIONS AND METHODS FOR PREVENTION AND TREATMENT OF MICROBIAL INFECTION

CROSS-REFERENCE TO RELATED APPLICATIONS

This application claims the benefit of priority to U.S. Provisional Application No. 63/129,941, filed on Dec. 23, 2020, which is incorporated herein by reference in its entirety.

FIELD OF THE DISCLOSURE

The present invention relates to microbial compositions containing *Lactobacillus*, and methods for reducing growth of microbes that cause infection in the body, including urogenital tract infection, and for treating or preventing the same using the compositions thereof.

BACKGROUND OF THE INVENTION

Urogenital tract infections are a common, often recurring health problem in humans (in both males and females), and animals. Urogenital tract infection can include acute or chronic urinary tract infection (UTI) (e.g., cystitis) and genital tract infection (e.g., vaginitis). Urogenital tract infection can be acute or chronic, symptomatic or asymptomatic, and can be sexually transmitted. Various microbial pathogens can cause urogenital tract infections, including Gram-negative bacteria (e.g., *Escherichia coli*), Gram-positive bacteria (e.g., *Staphylococcus saprophyticus*), Gram-variable bacteria (e.g., *Gardnerella vaginalis*), and yeasts (e.g., *Candida albicans*). These pathogens can also cause infection in other sites of the body.

It is generally understood that a healthy urinary tract is sterile. A healthy genital tract is populated by a normal microflora, which includes *Lactobacillus* species. In urogenital tract infection, an abnormal growth of pathogenic microbes is seen in the urogenital area, which can reduce or replace the normal microflora in the area.

The most common treatment for urogenital tract infection, and other infection caused by associated pathogens, is oral or topical administration of an antibiotic or anti-fungal medication to the affected subject. However, use of an antibiotic or anti-fungal medication can lead to the death of the normal flora in the urogenital tract, change in the flora profile, recurrent infections, and/or generation of drug-resistant pathogens. Moreover, the antibiotic or anti-fungal treatment may cause undesired side effects in the subject.

Therefore, there is a need for more effective, less harmful compositions and methods for treating and preventing infection, including urogenital tract infection, in humans and animals.

BRIEF SUMMARY OF THE INVENTION

The present disclosure describes microbial compositions containing Lactobacilli, and methods for reducing growth of microbes that cause infection in the body, including urogenital tract infection, and for treating or preventing the same using the compositions thereof.

In some aspects, a composition, comprising *Lactobacillus reuteri* 3613 (Lr3613), having been deposited under NRRL accession number B-67262, and/or *Lactobacillus reuteri* 3613-1 (Lr3613-1), having been deposited under NRRL accession number B-68035, and one or more of a component selected from the group consisting of an adjuvant, a carrier, and an excipient, wherein the component is pharmaceutically acceptable or nutritionally acceptable is disclosed herein. In one embodiment, the composition is a pharmaceutical composition, a dietetic composition, or a combination thereof. In specific embodiments, the adjuvant, carrier or excipient does not naturally occur with the *L. reuteri* 3613 and/or *L. reuteri* 3613-1.

In some embodiments, a concentration of the *Lactobacillus reuteri* 3613, the *Lactobacillus reuteri* 3613-1, or a combination of the *Lactobacillus reuteri* 3613 and the *Lactobacillus reuteri* 3613-1 in the composition is from $1\times10^6$ CFU/g to $1\times10^{10}$ CFU/g, from $1\times10^7$ CFU/g to $1\times10^9$ CFU/g, about $1\times10^7$ CFU/g, about $1\times10^8$ CFU/g, about $1\times10^9$ CFU/g, from $1\times10^6$ CFU/ml to $10\times10^{10}$ CFU/ml, from $1\times10^7$ CFU/ml to $1\times10^9$ CFU/ml, about $1\times10^7$ CFU/ml, about $1\times10^8$ CFU/ml, or about $1\times10^9$ CFU/ml. In particular embodiments, the concentration of *L. reuteri* 3613, *L. reuteri* 3613-1, or a combination of *L. reuteri* 3613 and *L. reuteri* 3613-1 is sufficient to reduce the growth and/or number of a pathogen disclosed herein. In specific embodiments, the pathogen is *Escherichia coli*, *Gardnerella vaginalis*, or a *Candida* species.

In some embodiments, the composition comprises a microbial culture. In one embodiment, the microbial culture is a lyophilized culture or a liquid culture.

In some embodiments, the composition comprises a pharmaceutically acceptable polysaccharide. In one embodiment, the composition comprises glycerol. In one embodiment, the *Lactobacillus reuteri* 3613 of the composition is in a 0.02% glycerol solution.

In some embodiments, the Lr3613 and/or Lr3613-1 bacterial strain composition disclosed herein is administered to a subject that is also administered (simultaneously or sequentially) a prebiotic. Prebiotics, such as those described elsewhere herein, may be combined with a bacterial strain of the invention into a formulated product or the prebiotic(s) may be administered separately from (before, during, or after) a bacterial strain of the invention.

In some embodiments, the composition is formulated as a food product or other edible material, such as water, oil, dairy product, milk, concentrated milk, yogurt, sour milk, frozen yogurt, *Lactobacillus* fermented beverage, milk powder, ice cream, cheese, soy milk, fruit juice, vegetable juice, sports drink, dessert, jelly, confectionery, baby food, health food, animal feed, herbal medicine, or dietary supplement. In one embodiment, the composition comprises cranberry juice.

In some aspects, the present disclosure describes a method of treating or preventing urogenital tract infection in a subject by administering a composition comprising an effective amount of *Lactobacillus reuteri* 3613, having been deposited under NRRL accession number B-67262, and/or *Lactobacillus reuteri* 3613-1 (Lr3613-1), having been deposited under NRRL accession number B-68035, to the subject.

In some embodiments, the effective amount of *Lactobacillus reuteri* 3613, *Lactobacillus reuteri* 3613-1, or a combination of *Lactobacillus reuteri* 3613 and *Lactobacillus reuteri* 3613-1 administered to the subject is from $1\times10^8$ CFU to $1\times10^{11}$ CFU, from $1\times10^9$ CFU to $1\times10^{10}$ CFU, or about $5\times10^9$ CFU per dose.

In some embodiments, the composition is administered once daily. In particular embodiments, the composition is administered once daily for a period of 2 days, 3 days, 5 days, 10 days to 120 days, 30 days, or 60 days.

In some embodiments, the urogenital tract infection is bacterial or fungal urinary tract infection, bacterial or fungal vaginitis, or both. In some embodiments, the pathogen is one or more of *Escherichia coli*, *Gardnerella vaginalis*, and a *Candida* species. The *Candida* species can include *Candida albicans*, *Candida krusei*, *Candida glabrata*, and *Candida tropicalis*.

In some embodiments, the urogenital tract infection is associated with one or more of *Lactobacillus* deficiency, chronic bacterial vaginosis, chronic yeast infection, chronic urinary tract infection, pregnancy, menopause, atrophic vaginitis, atrophic vaginosis, bacterial vaginosis in pregnancy, and vulva-vaginal candidiasis.

In some embodiments, the method for treating or preventing the urogenital tract infection comprises reducing growth of a pathogen that causes the urogenital tract infection. In some embodiments, the composition reduces growth of the pathogen, which includes one or more of a Gram-negative bacterium, a Gram-positive bacterium, a Gram-variable bacterium, and a fungus. The pathogen can be one or more of *Escherichia coli*, *Gardnerella vaginalis*, and a *Candida* species (e.g., *Candida albicans*, *Candida krusei*, *Candida glabrata*, and *Candida tropicalis*). In specific embodiments, the population of the pathogen is reduced by at least 5%, 10%, 15%, 20%, 25%, 30%, 40%, 50%, 60%, 70%, 75%, 80%, 85%, 90%, 91%, 92%, 93%, 94%, 95%, 96%, 97%, 98%, 99% or more following administration of an effective amount of the Lr3613 and/or Lr3613-1 bacterial composition.

In one embodiment, the composition of the method reduces growth of *Escherichia coli* by at least 97%. In another embodiment, the composition of the method reduces growth of *Gardnerella vaginalis* by at least 93%. In another embodiment, the composition of the method reduces growth of a *Candida* species by 98% or more.

In some embodiments, the composition of the method: (a) comprises reuterin; (b) comprises hydrogen peroxide; and/or (c) comprises lactic acid and regulates pH in the urogenital tract of the subject, thereby reducing growth of a pathogen that causes the urogenital tract infection. In specific embodiments, the *Lactobacillus reuteri* 3613 and/or *Lactobacillus reuteri* 3613-1 in the composition produces reuterin, hydrogen peroxide, and/or lactic acid. In some embodiments, the regulation of pH is lowering of pH, or regulating pH to pH of 4.2 in the urogenital tract of the subject.

In some embodiments, the subject is a male or female human. In other embodiments, the subject is an animal, such as a domestic or agricultural animal.

In some embodiments, administering the composition to the subject alleviates or prevents a symptom, sign, or condition associated with the urogenital tract infection. Symptoms, signs, or conditions that are alleviated or prevented may include one or more of: pain or burning sensation while urinating or during intercourse; frequent urination; urge to urinate despite having an empty bladder; urine that is bloody, cloudy, or foul-smelling; pressure or cramping in groin, lower abdomen, or back; pain, irritation, or itching in urogenital area; redness, swelling, rash, or pain in vagina or vulva; vaginal discharge that is irregular, watery, thick, white, green, yellow, or foul-smelling; fever; chills; asymptomatic or recurrent urogenital tract infection; bacterial vaginosis; preterm delivery caused by bacterial vaginosis in pregnancy; *Lactobacillus* deficiency; chronic bacterial vaginosis; chronic yeast infection; chronic urogenital tract infection in menopause; atrophic vaginitis; atrophic vaginitis; and vulva-vaginal candidiasis.

In some embodiments, the composition of the method is a pharmaceutical composition, a dietetic composition, or a combination thereof. The composition may further comprise one or more of a pharmaceutically acceptable adjuvant, a nutritionally acceptable adjuvant, a carrier, or an excipient.

In some embodiments, the method of the present invention comprises administering the composition via oral administration, rectal administration, vaginal administration, urinary tract or urinary bladder administration, or a combination thereof. The composition can be administered in a form of a solution, a suspension, an emulsion, a suppository, a lubricant, a capsule, a coated capsule, a gel, a paste, a tablet, a buccal tablet, a powder, a sachet, a troch, a pill, a syrup, a thick syrup, a chewable gum, a pearl, a pessary, a vial, a topical preparation, or a combination thereof.

In some embodiments, the composition further comprises an edible material, comprising water, oil, dairy product, milk, concentrated milk, yogurt, sour milk, frozen yogurt, *Lactobacillus* fermented beverage, milk powder, ice cream, cheese, soy milk, fruit juice, vegetable juice, sports drink, dessert, jelly, confectionery, baby food, health food, animal feed, herbal medicine, or dietary supplement. The composition may further comprise cranberry juice.

In one aspect, the present invention provides a method of reducing growth of a pathogenic microbe, comprising administering a composition comprising an effective amount of *Lactobacillus reuteri* 3613, having been deposited under NRRL accession number B-67262, and/or *Lactobacillus reuteri* 3613-1 (Lr3613-1), having been deposited under NRRL accession number B-68035. In some embodiments, the method comprises administering the composition to a subject, thereby reducing growth of a pathogenic microbe in the urogenital tract of the subject.

In some embodiments, the amount of *Lactobacillus reuteri* 3613, *Lactobacillus reuteri* 3613-1, or a combination of *Lactobacillus reuteri* 3613 and *Lactobacillus reuteri* 3613-1 to be administered is from $1\times10^8$ CFU to $1\times10^{11}$ CFU, from $1\times10^9$ CFU to $1\times10^{10}$ CFU, or about $5\times10^9$ CFU per dose. In some embodiments, the composition is administered once daily. In some embodiments, the composition is administered once daily for a period from 2 days, 3 days, 5 days, 10 days to 120 days, for 30 days, or for 60 days.

In some embodiments, the pathogenic microbe is one or more of a Gram-negative bacterium, a Gram-positive bacterium, a Gram-variable bacterium, and a fungus. In some embodiments, the pathogenic microbe is one or more of *Escherichia coli*, *Gardnerella vaginalis*, and a *Candida* species (e.g., *Candida albicans*, *Candida krusei*, *Candida glabrata*, and *Candida tropicalis*). In specific embodiments, the population of the pathogen is reduced by at least 5%, 10%, 15%, 20%, 25%, 30%, 40%, 50%, 60%, 70%, 75%, 80%, 85%, 90%, 91%, 92%, 93%, 94%, 95%, 96%, 97%, 98%, 99% or more.

In some embodiments, administering the composition reduces growth of *Escherichia coli* by at least 97%. In some embodiments, administering the composition of the reduces growth of *Gardnerella vaginalis* by at least 93%. In other embodiments, administering the composition reduces growth of a *Candida* species by 98% or more.

In some embodiments, administering the composition: (a) produces reuterin; (b) produces hydrogen peroxide; and/or (c) produces lactic acid and regulates pH, thereby reducing growth of the pathogenic microbe. In some embodiments, these effects take place in the urogenital tract of the subject. In specific embodiments, *Lactobacillus reuteri* 3613 and/or the *Lactobacillus reuteri* 3613-1 in the composition produces reuterin, hydrogen peroxide, and/or lactic acid.

In some embodiments, the regulation of pH is lowering of pH, or regulating pH to pH of 4.2 in the urogenital tract of the subject.

In one aspect, a kit comprising the composition disclosed herein, and optionally instructions for use is provided herein. In another aspect, the present disclosure describes a product comprising the composition disclosed herein. The product may be a pharmaceutical product, a vaginal suppository, a dairy product, a nutrition drink, a nutritional supplement, a health food, a nutrition feed, or a combination thereof.

All publications, patent applications, patents, and other references mentioned herein are incorporated by reference in their entirety.

The details of various embodiments of the disclosure are set forth in the description below. Other features, objects, and advantages of the disclosure will be apparent from the description and the drawings, and from the claims.

DETAILED DESCRIPTION

Figure 1:
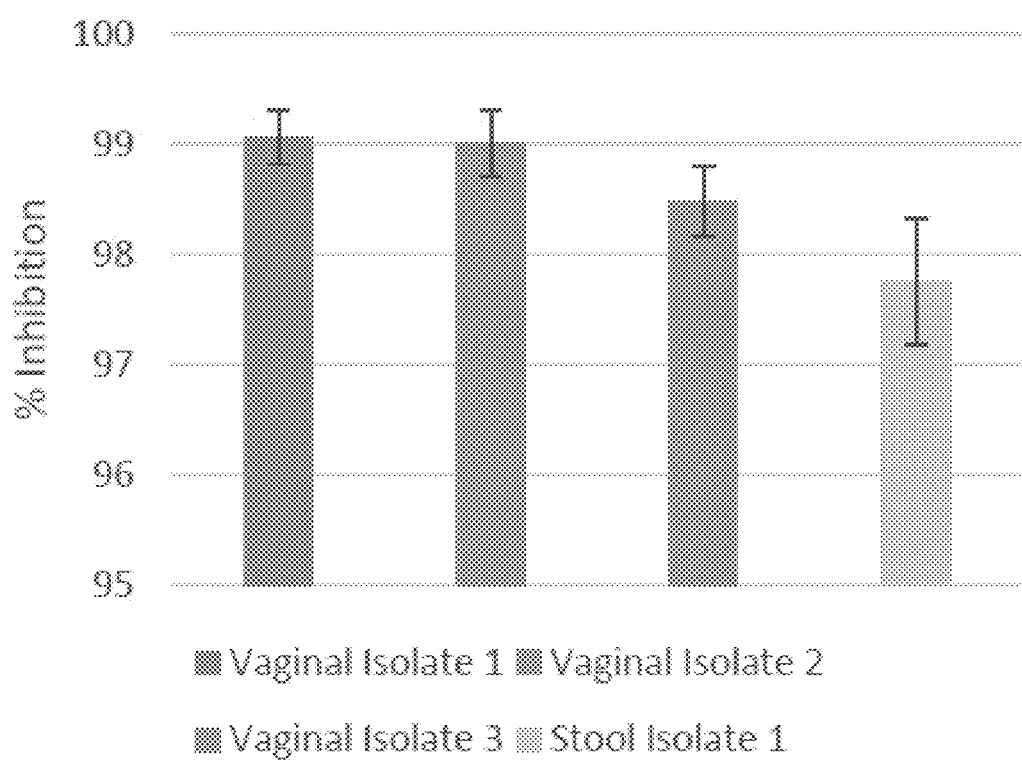
FIG. 1 shows growth inhibition of *Escherichia coli* isolated from vaginal and stool samples by *Lactobacillus reuteri* 3613-conditioned bacteriocin supernatant (i.e., culture supernatant of the respective bacteria cultured in MRS broth, and then incubated anaerobically in 0.02% glycerol solution to induce production of reuterin) (n=3).

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

I. Definitions

For convenience, the meaning of certain terms and phrases used in the specification, examples, and appended claims, are provided below. If there is an apparent discrepancy between the usage of a term in other parts of this specification and its definition provided in this section, the definition in this section shall prevail.

It must be noted that as used herein and in the appended claims, the singular forms "a," "and," and "the" include plural referents unless the context clearly dictates otherwise. Thus, for example, reference to "a sample" includes a plurality of such samples.

The term "about" when referring to a number or a numerical range means that the number or numerical range referred to is an approximation within experimental variability (or within statistical experimental error), and thus the number or numerical range may vary from, for example, between 1% and 15% of the stated number or numerical range.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values; however, inherently contain certain errors necessarily resulting from error found in their respective measurements.

The term "at least" prior to a number or series of numbers is understood to include the number adjacent to the term "at least", and all subsequent numbers or integers that could logically be included, as clear from context. When at least is present before a series of numbers or a range, it is understood that "at least" can modify each of the numbers in the series or range.

As used herein, "no more than" or "less than" is understood as the value adjacent to the phrase and logical lower values or integers, as logical from context, to zero. When "no more than" is present before a series of numbers or a range, it is understood that "no more than" can modify each of the numbers in the series or range.

As used herein, "up to" as in "up to 10" is understood as up to and including 10, i.e., 0, 1, 2, 3, 4, 5, 6, 7, 8, 9, or 10.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

The term "condition(s) associated with urogenital tract infection," as used herein, means any disease or condition that is associated with urogenital tract infection. Non-limiting examples of conditions associated with urogenital tract infection that are treatable or preventable using methods provided herein include: *Lactobacillus* deficiency; chronic bacterial vaginosis; chronic yeast infection; chronic urinary tract infection; menopause; atrophic vaginitis; atrophic vaginosis; bacterial vaginosis in pregnancy; preterm delivery of a fetus; vulva-vaginal candidiasis; pain or burning sensation while urinating or during intercourse; frequent urination; urge to urinate despite having an empty bladder; urine that is bloody, cloudy, or foul-smelling; pressure or cramping in groin, lower abdomen, or back; pain, irritation, or itching in urogenital area; redness, swelling, rash, or pain in vagina or vulva; vaginal discharge that is irregular, watery, thick, white, green, yellow, or foul-smelling; fever; and chills.

The terms "subject," and "patient" are used interchangeably herein, and generally refer to a mammal, including, but not limited to, primates, including simians and humans, equines (e.g., horses), canines (e.g., dogs), felines, various domesticated livestock (e.g., ungulates, such as swine, pigs, goats, sheep, and the like), as well as domesticated pets and animals maintained in zoos. Treatment and evaluation of humans is of particular interest.

As used herein, the term "diagnosis" can encompass determining the likelihood that a subject will develop a disease, or the existence or nature of disease in a subject. The term diagnosis, as used herein also encompasses determining the severity and probable outcome of disease or episode of disease or prospect of recovery, which is generally referred to as prognosis. In certain embodiments, the term "diagnosis" includes determining the likelihood that a subject will develop urogenital tract infection, such as a UTI or vaginitis.

As used herein, the terms "treat," "treatment," "treating," and the like, refer to obtaining a desired pharmacologic or physiologic effect. The effect may be therapeutic in terms of a partial or complete cure for a disease or an adverse effect attributable to the disease. The effect may be to prevent, delay, relieve, or alleviate at least one symptom associated with a disorder or a condition, or to slow or reverse the progression or anticipated progression of such a disorder or a condition.

"Treatment," as used herein, covers any treatment of a disease in a mammal, particularly in a human, and can include inhibiting the disease or condition, i.e., arresting its development; and relieving the disease, i.e., causing regression of the disease. "Treatment," as used herein, covers both prophylactic or preventive treatment (that prevent and/or slow the development of a targeted pathological condition or disorder) and curative, therapeutic or disease-modifying treatment. In certain embodiments, the term "treatment" can include inhibiting or preventing asymptomatic bacteriuria in a subject from progressing to a symptomatic urogenital tract infection.

As used herein, the terms "prevent," "prevention," "preventing," and the like, refer to avoiding or inhibiting the development of a targeted pathological condition or disorder, or at least one symptom associated thereof.

As used herein, "risk of urogenital tract infection" can refer to the likelihood or percent possibility of having a urogenital tract infection, for example, in comparison with a control subject.

As used herein, a "pharmaceutical composition" comprises an effective amount of a therapeutic agent (e.g. Lr3613 and/or Lr3613-1 bacterial composition disclosed herein).

The term "pharmaceutically acceptable" adjuvant, carrier, or excipient refers to a component that is an adjuvant, carrier, or excipient for administration of a therapeutic agent. Such components include, but are not limited to, saline, buffered saline, dextrose, water, glycerol, ethanol, and combinations thereof. For compositions administered orally, pharmaceutically acceptable adjuvants, carriers, and excipients include, but are not limited to inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract. Agents included in drug formulations are described further herein below. A pharmaceutically acceptable adjuvant, carrier, or excipient can be naturally or synthetic (e.g., non-naturally occurring).

As used herein, a "dietetic composition" means an edible composition, which may comprise a therapeutic agent. Typical dietetic compositions include foodstuffs that are commonly consumed by humans or animals.

The terms "probiotic" and "probiotics" as used herein can be used interchangeably and mean one or more natural, cultured, purified, genetically altered, and/or isolated strains of probiotic bacteria; products of probiotic bacteria; metabolites of probiotic bacteria; and mixtures, blends and combinations thereof that could confer health benefits on the host subject when administered in adequate amounts, more specifically, that beneficially affect a host by improving its urogenital system microbial balance, leading to effects on the health or well-being of the host, e.g., a reduction of problematic symptoms related to a urogenital tract infection. The probiotics of the present invention can be viable or non-viable when administered and/or when reaching the desired site of administration. The probiotics of the present invention can be administered together as a blend or mixture in a single dosage form, or can be administered in separate dosage forms at separate times.

The term "*Lactobacillus reuteri* strain 3613," as used herein, is used interchangeably with "Lr3613," "*L. reuteri* 3613," "*Lactobacillus reuteri* 3613," "Lr3613 bacterial composition," and other similar terms, refers to the corresponding bacteria, the corresponding composition, or the corresponding component of the composition.

The term "*Lactobacillus reuteri* strain 3613-1," as used herein, is used interchangeably with "Lr3613-1," "*L. reuteri* 3613-1," "*Lactobacillus reuteri* 3613-1," "Lr3613-1 bacterial composition," and other similar terms, refers to the corresponding bacteria, the corresponding composition, or the corresponding component of the composition.

Further, a "Lr3613 bacterial composition" and a "Lr3613 and/or Lr3613-1 bacterial composition" can refer to a composition comprising Lr3613, Lr3613-1, an active variant thereof, or a combination of any thereof, unless specifically described otherwise.

II. *Lactobacillus reuteri* 3613, *Lactobacillus reuteri* 3613-1, and Active Variants Thereof The present disclosure describes a composition comprising *Lactobacillus reuteri* 3613 (Lr3613) and/or *Lactobacillus reuteri* 3613-1 (Lr3613-1), with one or more of a pharmaceutically acceptable adjuvant, a nutritionally acceptable adjuvant, a carrier, and an excipient.

*Lactobacillus reuteri* can generally be found in the intestine of humans and animals and has the ability to produce lactic acid. In some embodiments, the production of acid by lactic acid bacteria, e.g., *Lactobacillus reuteri* of the present disclosure, causes the pH of their environment to decrease, creating a hostile environment for the growth of pathogenic microbes such as *Escherichia coli, Gardnerella vaginalis*, and *Candida* species. In certain embodiments, *Lactobacillus reuteri* 3613 and/or its active variant, e.g., *Lactobacillus reuteri* 3613-1 also has the ability to produce reuterin, a bacteriocin-like compound that has potent anti-microbial properties against a wide range of pathogens. Moreover, *Lactobacillus reuteri* 3613 and/or its active variant, e.g., *Lactobacillus reuteri* 3613-1 has the ability to produce an amount of hydroxyl peroxide sufficient to inhibit pathogens but does not affect the healthy micro biota of the urogenital tract. The reduction of pH in the urogenital tract, combined with the ability to produce reuterin and hydoxy peroxide confers *L. reuteri* 3613 and/or its active variant, e.g., *L. reuteri* 3613-1 an ability to prevent and control infection by pathogenic microbes, e.g., *Escherichia coli, Gardnerella vaginalis*, and *Candida* species in the body, including in the urogenital tract.

In certain embodiments, *Lactobacillus reuteri* 3613 of the present disclosure exhibits genetic characteristics set forth in Table 1 below. In some embodiments, *Lactobacillus reuteri* 3613 has intrinsic resistance to ciprofloxacin, tigecycline/ vancomycin, glycopeptides, and/or tetracycline. As used herein, "intrinsic resistance" refers to natural resistance that is not associated with mobile elements such as transposons or mutations and is not transferable. In some embodiments, *Lactobacillus reuteri* 3613 is susceptible to lincomycin at concentrations above 45 μg/ml, and is susceptible to tetracycline at 32 μg/mL.

In certain embodiments, *Lactobacillus reuteri* 3613-1 is a variant of *Lactobacillus reuteri* 3613, comprising an essentially identical chromosomal genome as *Lactobacillus reuteri* 3613. In some embodiments, both Lr3613 and Lr3613-1 can utilize D-ribose, D-galactose, D-glucose, D-maltose, D-lactose, D-melibiose, sucrose, D-raffinose, and potassium gluconate as carbon sources In certain embodiments, *Lactobacillus reuteri* 3613-1 of the present disclosure does not have an extrachromosomal plasmid that encodes the InuA gene, responsible for lincosamide (e.g., lincomycin) resistance, and is lincomycin sensitive. In some embodiments, the minimum inhibitory concentration (MIC) of lincomycin for Lr3613 and Lr3613-1 are >8 μg/ml and 1 μg/ml, respectively. In some embodiments, Lr3613-1 is substantially equivalent to Lr3613 with respect to the safety, the ability to produce lactic acid, the ability to reduce pH in the urogenital tract, the ability to produce reuterin, the ability to produce hydoxy peroxide, and/or the ability to prevent and control infection by pathogenic microbes, e.g., *Escherichia coli, Gardnerella vaginalis*, and *Candida* species in the body, including in the urogenital tract.

*Lactobacillus reuteri* 3613 was deposited with the Patent Depository of the National Center for Agricultural Utilization Research Agricultural Research Service, U.S. Department of Agriculture, 1815 North University Street, Peoria, Illinois 61604 U.S.A. on May 27, 2016 and assigned NRRL No. B-67262.

*Lactobacillus reuteri* 3613-1 was deposited with the Patent Depository of the National Center for Agricultural Utilization Research Agricultural Research Service, U.S. Department of Agriculture, 1815 North University Street, Peoria, Illinois 61604 U.S.A. on Jun. 3, 2021 and assigned NRRL No. B-68035.

Each of the deposits identified above will be maintained under the terms of the Budapest Treaty on the International Recognition of the Deposit of Microorganisms for the Purposes of Patent Procedure. Each deposit was made merely as a convenience for those of skill in the art and is not an admission that a deposit is required under 35 U.S.C. § 112.

A. Active Variants of a Bacterial Strain

Further provided are active variants of *Lactobacillus reuteri* 3613. As used herein, an "active variant" refers to a strain having all of the identifying characteristics of the recited strain. A "strain of the invention" includes active variants thereof. Active variants of the bacteria provided herein, e.g., *Lactobacillus reuteri* 3613, can be identified by employing, for example, methods that determine the sequence identity relatedness between the 16S ribosomal RNA, methods to identify groups of derived and functionally identical or nearly identical strains include Multi-locus sequence typing (MLST), concatenated shared genes trees, Whole Genome Alignment (WGA), Average Nucleotide Identity, and MinHash (Mash) distance metric.

In one aspect, the active variants of *Lactobacillus reuteri* 3613 include strains that are closely related to any of the disclosed strains by employing the Bishop MLST method of organism classification as defined in Bishop et al. (2009) *BMC Biology* 7(1)1741-7007-7-3. Thus, in specific embodiments, an active variant of a bacterial strain disclosed herein includes a bacterial strain that falls within at least an 80%, 85%, 86%, 87%, 88%, 89%, 90%, 91%, 92%, 93%. 94%, 95%, 96%, 97%, 98%, 98.5%, 98.8%, 99%, 99.1%, 99.2%, 99.3%, 99.4%, 99.5%, 99.6%, 99.7%, 99.8%, or 99.9% sequence cut off employing the Bishop method of organism classification as set forth in Bishop et al. (2009) *BMC Biology* 7(1)1741-7007-7-3, which is herein incorporated by reference in its entirety. Active variants of the bacteria identified by such methods will retain the ability to produce lactic acid, the ability to reduce pH in the urogenital tract, the ability to produce reuterin, and/or the ability to produce hydoxy peroxide.

In some embodiments, the active variant of *Lactobacillus reuteri* 3613 disclosed herein include strains that are closely related to *Lactobacillus reuteri* 3613 on the basis of the Average Nucleotide Identity (ANI) method of organism classification. ANI (see, for example, Konstantinidis, K. T., et al., (2005) *PNAS USA* 102(7):2567-72; and Richter, M., et al., (2009) *PNAS* 106(45):19126-31) and variants (see, for example, Varghese, N.J., et al., *Nucleic Acids Research* (Jul. 6, 2015): gkv657) are based on summarizing the average nucleotides shared between the genomes of strains that align in WGAs. Thus, in specific embodiments, an active variant of bacterial strain *Lactobacillus reuteri* 3613 disclosed herein includes a bacterial strain that falls within at least a 90%, 95%, 96%, 97%, 97.5%, 98%, 98.5%, 98.8%, 99%, 99.5%, or 99.8% sequence cut off employing the ANI method of organism classification as set forth in Konstantinidis, K. T., et al., (2005) *PNAS USA* 102(7):2567-72, which is herein incorporated by reference in its entirety. Active variants of the bacteria identified by such methods will retain the ability to produce lactic acid, the ability to reduce pH in the urogenital tract, the ability to produce reuterin, and/or the ability to produce hydoxy peroxide.

In particular embodiments, the active variants of the isolated bacterial strain(s) disclosed herein include strain(s) that are closely related to *Lactobacillus reuteri* 3613 on the basis of 16S rDNA sequence identity. See Stackebrandt E, et al., "Report of the ad hoc committee for the re-evaluation of the species definition in bacteriology," *Int J Syst Evol Microbiol.* 52(3):1043-7 (2002) regarding use of 16S rDNA sequence identity for determining relatedness in bacteria. In an embodiment, the active variant is at least 95% identical to any of the above strains on the basis of 16S rDNA sequence identity, at least 96% identical to any of the above strains on the basis of 16S rDNA sequence identity, at least 97% identical to any of the above strains on the basis of 16S rDNA sequence identity, at least 98% to any of the above strains on the basis of 16S rDNA sequence identity, at least 98.5% identical to any of the above strains on the basis of 16S rDNA sequence identity, at least 99% identical to any of the above strains on the basis of 16S rDNA sequence identity, at least 99.5% to any of the above strains on the basis of 16S rDNA sequence identity or at least 100% to any of the above strains on the basis of 16S rDNA sequence identity. Active variants of the bacteria identified by such methods will retain the ability to produce lactic acid, the ability to reduce pH in the urogenital tract, the ability to produce reuterin, and/or the ability to produce hydoxy peroxide.

The MinHash (Mash) distance metric is a comparison method that defines thresholds for hierarchical classification of microorganisms at high resolution and requires few parameters and steps (Ondov et al. (2016) *Genome Biology* 17:132). The Mash distance estimates the mutation rate between two sequences directly from their MinHash sketches (Ondov et al. (2016) *Genome Biology* 17:132). Mash distance strongly corresponds to Average Nucleotide Identity method (ANI) for hierarchical classification (See, Konstantinidis, K. T. et al. (2005) *PNAS USA* 102(7):2567-72, herein incorporated by reference in its entirety). That is, an ANI of 97% is approximately equal to a Mash distance of 0.03, such that values put forth as useful classification thresholds in the ANI literature can be directly applied with the Mash distance.

Active variants of the bacterial strain(s) disclosed herein include strains that are closely related to *Lactobacillus reuteri* 3613 on the basis of the Minhash (Mash) distance between complete genome DNA sequences. Thus, in specific embodiments, an active variant of a bacterial strain disclosed herein includes bacterial strains having a genome within a Mash distance of less than about 0.015 to the disclosed strains. In other embodiments, an active variant of a bacterial strain disclosed herein includes a distance metric of less than about 0.001, 0.0025, 0.005, 0.010, 0.015, 0.020, 0.025, or 0.030. A genome, as it relates to the Mash distance includes both bacterial chromosomal DNA and bacterial plasmid DNA. In other embodiments, the active variant of a bacterial strain has a genome that is above a Mash distance threshold to the disclosed strains that is greater than dissimilarity caused by technical variance. In further instances, the active variant of a bacterial strain has a genome that is above a Mash distance threshold to the disclosed strains that is greater than dissimilarity caused by technical variance and has a Mash distance of less than about 0.015. In other instances, the active variant of a bacterial strain has a genome that is above a Mash distance threshold to the disclosed strains that is greater than dissimilarity caused by technical variance and has a Mash distance of less than about 0.001, 0.0025, 0.005, 0.010, 0.015, 0.020, 0.025, or 0.030.

III. Pharmaceutical and/or Nutritional Compositions Comprising *Lactobacillus reuteri* 3613, *Lactobacillus reuteri* 3613-1, and/or Active Variants Thereof The present disclosure provides a composition comprising *Lactobacillus reuteri* 3613 (Lr3613), *Lactobacillus reuteri* 3613-1 (Lr3613-1), and/or an active variant thereof, with one or more of a pharmaceutically acceptable adjuvant, a nutritionally acceptable adjuvant, a carrier, and an excipient. The composition may be a pharmaceutical composition, a dietetic composition, or a combination thereof.

The present disclosure further relates to dietetic or pharmaceutical compositions based on microbial cultures of Lr3613 and/or Lr3613-1, including lyophilized cultures or liquid cultures such as yogurt and other fermented and/or non-fermented drinks. A concentration of the *Lactobacillus reuteri* 3613, the *Lactobacillus reuteri* 3613-1, or a combination of the *Lactobacillus reuteri* 3613 and the *Lactobacillus reuteri* 3613-1 in the composition may be from $1 \times 10^6$ CFU/g to $1 \times 10^{10}$ CFU/g, from $1 \times 10^7$ CFU/g to $1 \times 10^9$ CFU/g, about $1 \times 10^7$ CFU/g, $1 \times 10^8$ CFU/g, about $1 \times 10^9$ CFU/g, from $1 \times 10^6$ CFU/ml to $1 \times 10^{10}$ CFU/ml, from $1 \times 10^7$ CFU/ml to $1 \times 10^9$ CFU/ml, about $1 \times 10^7$ CFU/ml, about $1 \times 10^8$ CFU/ml, or about $1 \times 10^9$ CFU/ml.

The composition of the present invention may comprise a pharmaceutically acceptable polysaccharide, such as glycerol. In one embodiment, the composition comprises *Lactobacillus reuteri* 3613 and/or *Lactobacillus reuteri* 3613-1 in a 0.02% glycerol solution. Glycerol can induce Lr3613 and/or Lr3613-1 to produce reuterin, an anti-microbial compound as disclosed elsewhere herein.

Compositions of the invention may also include prebiotics, which may be combined or mixed with a formulated Lr3613 and/or Lr3613-1 composition disclosed herein into a feed or food composition, into drinking water, or into a pharmaceutical composition. Prebiotics are food ingredients that are not readily digestible by enzymes endogenous to the gut (such as those expressed by the animal or those expressed by the resident gut microbiome) and that selectively stimulate the growth and activity of selected groups of intestinal microorganisms that confer beneficial effects upon their host, such as Lr3613 and/or Lr3613-1. Typically, it is beneficial microorganism populations that benefit from the presence of prebiotic compounds. Prebiotics can consist of oligosaccharides and other small molecules that serve as metabolic substrates for growth of beneficial microbes. In some embodiments, the prebiotics of the compositions of the present disclosure include galacto-oligosaccharides, fructo-oligosaccharides, inulin, isomalto-oligosaccharies, gentio-oligosaccharides, lactilol, lactosucrose, lactulose, xylosucrose, glycosyl sucrose, pyrodextrins, soybean oligosaccharides, guar gum, locust bean gum, arabinan, galactan, pectins, and pectic polysaccharides. While many diverse microbes inhabit the intestinal tract of a host organism, prebiotic compounds are only utilized by the beneficial microbes and lead to a selective enhancement of the beneficial microbe population. In some embodiments, the present disclosure provides compositions having a formulation that includes both prebiotics and probiotics, which may be referred to as a "synbiotic".

The compositions according to the present invention may comprise additional nutritional components including but not limited to the following components: vitamins, antioxidants (e.g., preparations from pomegrenade or soybean flavonoids), fibers (inulin and fructooligosaccharides), mineral salts, phytoderivatives, water, oil, milk, concentrated milk, yogurt, sour milk, frozen yogurt, *Lactobacillus* fermented beverage, milk powder, ice cream, cheese, soy milk, fruit juice, vegetable juice, sports drink, dessert, jelly, confectionery, baby food, health food, animal feed, herbal medicine, or dietary supplement. In a particular embodiment, the composition comprises cranberry juice in addition to *Lactobacillus reuteri* 3613 and/or *Lactobacillus reuteri* 3613-1.

IV. Methods of Treating Urogenital Tract Infection

A method of treating or preventing infection in a subject, including urogenital tract infection, by administering a composition comprising an effective amount of *Lactobacillus reuteri* 3613, *Lactobacillus reuteri* 3613-1, and/or an active variant thereof to the subject is provided herein. In some embodiments, the subject is a male or female human. In other embodiments, the subject is an animal, such as a domestic animal or agricultural livestock animal.

A. Urinary Tract Infection or Conditions Associated with Urinary Tract Infection In some embodiments, a method of treating or preventing urinary tract infection in a subject, comprising administering an effective amount of *L. reuteri* 3613, *L. reuteri* 3613-1, and/or an active variant thereof to the subject, is provided. A urinary tract infection (UTI) is an infection of any part of the urinary tract. The urinary tract includes the kidneys, the bladder, the urethra, and the ureter. UTIs are one of the most frequently seen infectious diseases in the United States making up 7 million patient visits per year.

UTIs typically result in a variety of symptoms, depending on the specific site of infection. Infection of the kidneys (e.g., acute pyelonepthritis) can result in upper back and side pain, high fever, shaking and chills, nausea, and vomiting. Infection of the bladder (e.g., cystitis) can result in pelvic pressure, lower abdomen discomfort, frequent and painful urination, and blood in the urine. Infection of the urethra (e.g., urethritis) typically includes a burning sensation associated with urination. For febrile UTI, a fever will be present, and possibly other associated symptoms such as shaking and chills as well. If left untreated, UTIs can lead to severe bladder and kidney infections and sepsis.

Urinary tract infections can be acute or chronic. An acute UTI is typically short term (i.e., less than one month) and of high intensity, whereas a chronic infection is a longer-term infection (i.e., lasting at least one month, and up to a number of years) that typically does not respond to antimicrobial treatment. In a colonization (i.e., asymptomatic bacteriuria), the patient typically has bacteria growing in their bladder but they do not have symptoms typically associated with a urinary tract infection. An acute infection is present when the patient has symptoms such as painful urination or fever. A fever, as defined herein, is a body temperature above 100.4. degree. Fahrenheit. If an acute infection is present simultaneously with a chronic infection, the effects of the acute infection will dominate those of the chronic infection in terms of overall characterization of the infection, for at least the reason that a chronic infection typically shows few effects.

Urinary Pathogenic *Escherichia coli* (UPEC) accounts for 75% of all UTIs. UPEC's primary reservoir is in the gastrointestinal tract. It is hypothesized that the *Escherichia coli* is excreted in feces and is able to make its way into the urethra and bladder. Other pathogens that cause UTI include a variety of Gram-negative, Gram-positive, and Gram-variable bacteria, including *Gardnerella vaginalis, Pseudomonas, Enterococcus, Enterobacter, Klebsiella*, or *Proteus mirabilis*. UTI can also occur as a result of infection by pathogens other than bacteria. For example, urinary tract infections can also be caused by viruses and fungi, such as yeasts. Fungal UTI is commonly caused by infection by fungi of the genus *Candida*. Examples of viral UTI include those by BK virus, cytomegalovirus (CMV) and Epstein-Barr virus (EBV). Risk factors for UTI includes female anatomy, sexual activity, use of diaphragms for birth control. Menopause, kidney stones, prostate hypertrophy, immune suppression, catheter use, and a recent urinary procedure. The urogenital tract infection is diagnosed using analysis of a sample from the subject (e.g., a urine sample).

Antibiotics are currently the primary treatment for urinary tract infections, but they are not always effective at clearing the infection. Twenty-seven percent of women experience a recurring infection within 6 months of antibiotic treatment and 2.7% will experience a third recurrence. Accordingly, provided herein is the use of *L. reuteri* 3613 and/or its active variant (e.g., *L. reuteri* 3613-1) to treat urinary tract infections comprising administering an effective amount of *L. reuteri* 3613 and/or its active variant (e.g., *L. reuteri* 3613-1). In some embodiments, a composition comprising *L. reuteri* 3613 and/or its active variant (e.g., *L. reuteri* 3613-1) can be administered as a monotherapy. Alternatively, the composition comprising *L. reuteri* 3613 and/or its active variant (e.g., *L. reuteri* 3613-1) can be administered in combination with a second therapy, e.g., antibiotics, as further descried elsewhere in the present disclosure.

B. Genital Tract Infections

Methods of treating or preventing genital tract infection in a subject comprising administering an effective amount of *L. reuteri* 3613, *L. reuteri* 3613-1, and/or an active variant thereof to the subject are disclosed herein. The healthy human vagina is populated by a variety of *Lactobacillus* species, which play an essential role in protecting women from urogenital infection. Lactobacilli have the ability to adhere to vaginal epithelia, to inhibit the adhesion and growth of pathogens, deplete nutrients otherwise available to pathogens, and modulate the host immune response and microenvironment. Most importantly, Lactobacilli can metabolize the glycogen contained in the cells of the vaginal vault, forming lactic acid as the final product. Thus, in a healthy vagina, pH-values of 4.0-4.5 are reached, a level at which many pathogens cannot flourish. Several species of Lactobacillus have been described to populate the vagina to varying degrees, including L. acidophilus, L. fermentum, L. brevis, L. jensenii, L. casei, L. crispatus, L. gasseri, L. iners, L. jensenii, L. acidophilus, and L. rhamnosus.

Infectious vaginitis results from increased infection of non-single pathogenic bacteria that prefers basic environment due to elevated vaginal pH and is usually accompanied by a reduction of the normal Lactobacillus flora (probiotic) in the vagina. The common pathogens include Gardnerella species, Escherichia coli, Candida albicans, Candida tropicalis, Streptovecido vaginalis, and Neisseria, Prevotella, Proteus, Bacteroides, Mobiluncus, and Trichomonas species (Mastromarino P. et al., 2013, New microbiologica, 36, 229-238; Srinivasan S. et al., 2008, The Human Vaginal Bacterial Biota and Bacterial Vaginosis, Interdisciplinary Perspectives on Infectious Diseases, Vol., 2008, Article ID 750479, p 1-3).

Gardnerella vaginalis is a bacterium found in the vaginal tract of most women, but increased levels of G. vaginalis can lead to bacterial vaginosis. Bacterial vaginosis is a polymicrobial disorder of the vaginal microflora strongly associated with G. vaginalis. G. vaginalis produces a cytolysin, vaginolysin, which assists in the initial colonization in host epithelial cells. Once attached, G. vaginalis has the ability to form a biofilm which allows for increased survival against host immune mechanisms as well as antibiotic treatments.

Genital tract infection including bacterial vaginosis is associated with symptoms including itching and order of the affected area, and abnormal discharge. Vaginal infection including bacterial vaginosis can lead to preterm birth, endometritis, pelvic inflammatory disease, reproductive tract infections, and preterm labor. Genital tract infection can be transmitted sexually (i.e., sexually-transmitted disease).

Risk factors for genital tract infection include sexual activity, and genitourinary atrophy associated with menopause. During menopause, involution of the female genital tract occurs, reflecting possibly a built-in biologic life expectancy interrelated with the neurohypophyseal endocrine axis. The major universal change is vaginal atrophy. Vaginal dryness, burning, itching and dyspareunia are frequent complaints along with dysuria, urinary frequency and recurrent infections. The genitourinary atrophy following menopause is associated with a decline in estrogen secretion accompanied by depletion of Lactobacilli and increased colonization by pathogenic microorganisms associated with bacterial vaginosis and urinary tract infections. In postmenopausal women, vaginal estriol therapy reduces E. coli colonization and increases the numbers of Lactobacilli, with the result that the incidence of recurrent urinary and genital tract infections drops significantly Two methods are available for diagnosis of bacterial vaginosis: (1) Amsel criteria, in which identification of three out of the four following clinical symptoms will give a confirmed diagnosis: watery, gray, and white vaginal discharge attached to the vaginal wall; the vaginal pH is greater than 4.5; Whiff test: the discharge has a foul ammonia smell (foul-smelling fishy odor) in the presence of 10% KOH; the smear specimen shows a large number of bacteria adsorbed in the vaginal epithelial cells under the microscope and the cells are granular or clue cells with dotted appearance; (2) Nugent score, a Gram stain scoring system for vaginal swab: a Nugent score ≥7 or 4-7 along with the presence of clue cells in the specimens will give a confirmed diagnosis of bacterial vaginosis.

The most common treatment of genital tract infection is oral or topical administration of antibiotics, such as Metronidazole. However, use of antibiotics not only kills the pathogens, but also leads to the death of the normal flora in the genital tract. In addition, the growth of probiotic bacteria in the body is usually slower than pathogens and therefore medication usually will result in decreased immunity of patients which consequently changes the genital tract bacterial patterns in the patients and leads to repeated infections or even interferes with the treatment by generating drug-resistant pathogens. Moreover, there is also a potential risk of side effects of drugs. Despite the treatment of Metronidazole has significant clinical efficacy, there is still a relapse rate as high as 50% and the inevitable drawbacks of the antibiotics, and these are difficult problems that need to be addressed. Hence, searching for alternative drugs or treatments that have no side effects, higher efficacy and reduced recurrence is the major topic in the recent studies associated with genital tract infection and bacterial vaginosis (Hongying T. et al., Archives of Gynecology and Obstetrics, 2017, 295, 1331-1339).

Lactobacillus replacement treatment can be used to be effective orally or by the use of a suppository, e.g., L. rhamnosus GR-1 (ATCC 55826), L. reuteri RC-14 (ATCC 55845), L. crispatus LBV 88 (DSM 22566), L. rhamnosus LBV 96 (DSM 22560), L. jensenii LBV 116 (DSM 22567), L. gasseri LBV 150N (DSM 22583), L. crispatus LBV 10 (DSM 23744), L. crispatus LBV 61 (DSM 23745), L. jensenii LBV 8 (DSM 23746) L. jensenii LBV 110 (DSM 23747), L. rhamnosus LBV 69 (DSM 23748), L. rhamnosus LBV 136 (DSM 23749), L. gasseri LBV 162 (DSM 23750) and L. gasseri LBV 62 (DSM 23751). Lactobacilli can utilize either hydrogen peroxide, biofilm formation, or undetermined mechanisms to control pathogens. In some embodiments, any of the treatment described herein can be combined as a second therapy with the therapy comprising administering a composition comprising L. reuteri 3613 and/or its active variant (e.g., L. reuteri 3613-1). Alternatively, a composition comprising L. reuteri 3613 and/or its active variant (e.g., L. reuteri 3613-1) can be administered as a monotherapy.

C. Candidiasis

In some embodiments, the present disclosure relates to a method of treating or preventing candidiasis in a subject comprising administering an effective amount of L. reuteri 3613 and/or its active variant (e.g., L. reuteri 3613-1) to the subject. Candida is a fungus that is commonly found on the skin or in mucous membranes such as the vagina or mouth on the human body. While Candida species are often considered normal flora, they have the ability to overgrow and cause disease, candidiasis. According the CDC, about 75% of women will have a vaginal yeast infection in their lifetime. Candidiasis (i.e., Candida infection) often occurs in people who have a weakened immune system, are taking antibiotics which cause disruption of the normal microbiota or are taking medications that cause a reduction in mucus production or drying of mucus membrane areas.

One of the most common types of candidiasis is infection of the vagina, more commonly known as a yeast infection.

Vaginal candidiasis is the second leading cause of vaginal infection, affecting more than 200,000 women per year in the United States. Eighty to 85 percent of vaginal candidiasis is caused by *Candida albicans*. While this is the main clinical isolate, *Candida tropicalis, Candida glabrata*, and *Candida krusei* have also been associated with vaginal candidiasis.

Anti-fungal medication is given to treat Candidiasis, but many patients or subjects experience recurring infections and need repeated treatment, e.g., up to three times per year for treatment of vaginal *Candida* infection, indicating an important need for prevention of infection. In some embodiments, any of the treatment described herein can be combined as a second therapy with the therapy comprising administering a composition comprising *L. reuteri* 3613 and/or its active variant (e.g., *L. reuteri* 3613-1). Alternatively, a composition comprising *L. reuteri* 3613 and/or its active variant (e.g., *L. reuteri* 3613-1) can be administered as a monotherapy.

D. Administration Dosages, Compositions, Routes, and Timing

As used herein an "effective amount" or "therapeutically effective amount" refers to a quantity of a bacterial strain composition comprising a bacterial strain of the invention that decreases the growth or amount of at least pathogen as disclosed herein. In specific embodiments, the population of the pathogen is reduced by at least 5%, 10%, 15%, 20%, 25%, 30%, 40%, 50%, 60%, 70%, 75%, 80%, 85%, 90%, 91%, 92%, 93%, 94%, 95%, 96%, 97%, 98%, 99% or more. When administered to a subject, an effective amount or therapeutically effective amount of Lr3613, Lr3613-1, an active variant thereof, or a combination of any thereof described herein reduces or alleviates at least one symptom of the health problems, conditions, and/or diseases managed by the methods and of the present invention. In specific embodiments, an effective amount of Lr3613 reduces or alleviates at least one symptom of a urinary tract infections, genital tract infection, and/or candidiasis. In specific embodiments, the symptom is reduced by at least 5%, 10%, 15%, 20%, 25%, 30%, 40%, 50%, 60%, 70%, 75%, 80%, 85%, 90%, 91%, 92%, 93%, 94%, 95%, 96%, 97%, 98%, 99% or more.

Lr3613, Lr3613-1, an active variant thereof, or a combination of any thereof can be administered at a dose of from about $1\times10^3$ to about $1\times10^{14}$ CFU, alternatively from about $1\times10^5$ to about $1\times10^{14}$ CFU, alternatively from about $1\times10^7$ to about $1\times10^{14}$ CFU, alternatively from about $1\times10^9$ to about $1\times10^{12}$ CFU, alternatively from about $1\times10^{10}$ to about $1\times10^{12}$ CFU, alternatively from about $1\times10^{11}$ to about $1\times10^{12}$ CFU, alternatively from about $1\times10^8$ CFU to about $1\times10^{11}$ CFU, or alternatively from about $1\times10^9$ CFU to about $1\times10^{10}$ CFU per day. In specific embodiments, Lr3613 can be administered at a dose of about $5\times10^9$ CFU per day.

The composition comprising Lr3613, Lr3613-1, and/or an active variant thereof can be administered daily, every other day, every two days, or as often or seldom as desired to achieve alleviation of symptoms. The probiotic can be administered in a single unit dose administered at any time during a day. Alternatively, the composition can be administered in two or more doses administered at a single time of day or at two or more separate times of day. In some preferred embodiments, the composition is administered once daily. In some embodiments, the composition is administered once daily for a period of 2 days, 3 days, 5 days, 7 days, 10 days to 120 days, and preferably for 30 days, or for 60 days.

Lr3613, Lr3613-1, and/or an active variant thereof in the composition of the present invention can be viable or non-viable when administered and/or when reaching the desired site of administration. Lr3613, Lr3613-1, and/or an active variant thereof of the present invention can be administered together as a blend or mixture in a single dosage form, or can be administered in separate dosage forms at separate times. In specific embodiments, a spent culture supernatant of Lr3613, Lr3613-1, and/or an active variant thereof can be used in the compositions disclosed herein. The supernatant can comprise bacteriocins (e.g., reuterin, acids, and peroxide compounds)

The Lr3613 and/or Lr3613-1 bacterial composition can be incorporated into a unit dosage form. Application forms of the compositions according to the disclosure herein include those suitable for oral intake or topical urogenital administration. Non-limiting examples of dosage forms of into which the Lr3613 and/or Lr3613-1 bacterial composition and any additional material such as a carrier can be incorporated include capsule, coated capsule, chewable tablet, swallowable tablet/pill, buccal tablet, coated tablet, troche, powder, lozenge, soft chew, chewable gum, solution, suspension, emulsion, spray, extract, tincture, oil, decoction, infusion, syrup, thick syrup, elixir, wafer, vial, suppository, pearl, pessary, food product, and combinations thereof. The dosage forms can comprise ingestible carriers, adjuvants, or excipients in natural or non-natural forms. Non-limiting examples of which include natural or non-natural solid or liquid filler diluents, encapsulating substances, and mixtures and combinations thereof; sugars; starches; cellulose and its derivatives; powdered tragacanth; malt; gelatin; talc; stearic acid; magnesium stearate; vegetable oils; polyols; agar; gel; paste; alginic acid; pyrogen-free water; isotonic saline; phosphate buffer solutions; wetting agents; lubricants; coloring agents; flavoring agents; preservatives; and combinations thereof.

The composition may be a pharmaceutical composition, a dietetic composition, or combinations thereof. The composition may be administered orally, vaginally, or rectally, or instilled into the urinary tract or the bladder. When administered orally, Lr3613, Lr3613-1, and/or their active variant is expected to survive the passage through the gastrointestinal tract (e.g., stomach, duodenum) displaying a certain stability towards acid and bile, and temporarily colonize the gut. From there, Lr3613, Lr3613-1, and/or their active variant may ascend to the urogenital area, e.g., vagina, and colonize the urogenital mucosa. When Lr3613, Lr3613-1, and/or their active variant is administered via bladder, urinary tract, rectal, or vaginal instillation, e.g., as vaginal capsules or suppositories, it can also colonize the urogenital tract. Colonization of the gut, gastrointestinal tract, urogenital tract, or other mucosal layers of a subject by Lr3613, Lr3613-1, and/or their active variant can be temporary or stable for more than 1 week, 2 weeks, 3 weeks, 4 weeks, 2 months, 3 months, 6 months, 1 year, or more.

The composition further may comprise or be in the form of an edible material, such as water, oil, dairy product, milk, concentrated milk, yogurt, sour milk, frozen yogurt, *Lactobacillus* fermented beverage, milk powder, ice cream, cheese, soy milk, fruit juice, vegetable juice, sports drink, dessert, jelly, confectionery, baby food, health food, animal feed, herbal medicine, or dietary supplement. In specific embodiments, the Lr3613 and/or Lr3613-1 bacterial composition comprises cranberry juice and or is administered along with cranberry juice. The administration of cranberry juice along with the Lr3613 and/or Lr3613-1 bacterial composition can be simultaneous or sequential with either the bacterial composition or the cranberry juice being administered first.

In some embodiments, the Lr3613 and/or Lr3613-1 bacterial composition is self administered, or administered with caregiver assistance, and does not require a medical professional's presence. In specific embodiments, standardized instructions on preparation and administration, including a tutorial on use of the therapeutic probiotics and/or a step by step video can be provided to the subject.

E. Mechanisms of Action

The present disclosure discloses protective and therapeutic effects of Lactobacilli against potential pathogens in the urogenital area and in the body, which can be generated through the metabolic activity of the Lr3613, Lr3613-1, and/or their active variant, generating multiple unrelated inhibitory metabolites. The Lr3613 and/or Lr3613-1 bacterial composition of the present disclosure can exert its protective and therapeutic effects through at least any of the three following modes of action. First, the bacteria consume glycogen and other sources of glucose and is capable of producing lactic acid. The low pH generated in this manner can be harmful to the less desirable bacteria and fungi and thus protects the vaginal mucosa, the urogenital tract, or other sites in the body against infections. The composition may regulate pH to pH of 4.2 in the urogenital tract of the subject, or when desirable, in other sites of the body.

Second, in some embodiments, the Lr3613 and/or Lr3613-1 bacterial composition can produce a bacteriocin, such as reuterin. Reuterin is a compound that has antimicrobial effect against a variety of microbes, including Gram-negative bacteria, Gram-positive bacteria, Gram-variable bacteria, and fungi, including yeasts.

Third, in some embodiments the Lr3613 and/or Lr3613-1 bacterial composition comprising Lr3613, Lr3613-1, and/or their active variant can produce hydrogen peroxide. Hydrogen peroxide can be effective at inhibiting pathogens such as *E. coli* and *Gardnerella vaginalis* and *Candida albicans*, but often does not affect the healthy micro biota of the urogenital tract.

The Lr3613 and/or Lr3613-1 bacterial composition of the present disclosure may be capable of acting through at least all of these three mechanisms of action simultaneously to treat or prevent infection, including urogenital infection, in a subject.

F. Therapeutic Effect

Methods for treating or preventing pathogen infection, including urogenital tract infection, which may be bacterial or fungal urinary tract infection, bacterial or fungal vaginitis, or both are provided herein. The pathogen may be one or more of *Escherichia coli*, *Gardnerella vaginalis*, a *Candida* species, or any other bacterial or fungal species that results in urinary tract infections or genital tract infections. The *Candida* species may include *Candida albicans*, *Candida krusei*, *Candida glabrata*, and *Candida tropicalis*. The method of the present invention may reduce growth of a pathogen that causes the urogenital tract infection, including one or more of a Gram-negative bacterium, a Gram-positive bacterium, a Gram-variable bacterium, and a fungus. The pathogen can be one or more of *Escherichia coli*, *Gardnerella vaginalis*, and a *Candida* species (e.g., *Candida albicans*, *Candida krusei*, *Candida glabrata*, and *Candida tropicalis*).

In some embodiments, the growth rate or absolute numbers of the pathogen is reduced following administration of the Lr3613 and/or Lr3613-1 bacterial composition. For example, the growth rate of the pathogen can be reduced by about 10-100%, 20-100%, 30-100%, 40-100%, 50-100%, 60-100%, 70-100%, 80-100%, 20-90%, 30-90%, 40-90%, 50-90%, 60-90%, or 70-90% (e.g., by about 10-20%, 20-30%, 30-40%, 40-50%, 50-60%, 60-70%, 70-80%, 80-90%, or 90-100%), e.g., by about 10%, 15%, 20%, 25%, 30%, 35%, 40%, 45%, 50%, 55%, 60%, 65%, 70%, 75%, 80%, 85%, 90%, 95%, or 100%, or by at least 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% relative to the rate prior to administration of the Lr3613 and/or Lr3613-1 bacterial composition. Growth rate can be measured by standard methods known in the art, e.g., by analyzing data obtained by real time PCR, turbidimetry, or a hemocytometer. Similarly, the amount (e.g., absolute number) of the pathogen can be reduced following administration of the Lr3613 and/or Lr3613-1 bacterial composition. For example, the amount of the pathogen can be reduced by about 10-100%, 20-100%, 30-100%, 40-100%, 50-100%, 60-100%, 70-100%, 80-100%, 20-90%, 30-90%, 40-90%, 50-90%, 60-90%, or 70-90% (e.g., by about 10-20%, 20-30%, 30-40%, 40-50%, 50-60%, 60-70%, 70-80%, 80-90%, or 90-100%), e.g., by about 10%, 15%, 20%, 25%, 30%, 35%, 40%, 45%, 50%, 55%, 60%, 65%, 70%, 75%, 80%, 85%, 90%, 95%, or 100%, or by at least 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% relative to the amount prior to administration of the Lr3613 and/or Lr3613-1 bacterial composition. The amount of the pathogen can be measured by standard methods known in the art, e.g., by analyzing data obtained by real time PCR, turbidimetry, or a hemocytometer.

In certain embodiments, the methods of the present invention may reduce growth (e.g., growth rate or amount) of *Escherichia coli* by at least 90%, at least 95%, at least 96%, or at least 97%; reduce growth (e.g., growth rate or amount) of *Gardnerella vaginalis* by at least 90%, at least 91%, at least 92%, or at least 93%; reduce growth (e.g., growth rate or amount) of a *Candida* species by at least 90%, at least 95%, at least 96%, at least 97%, at least 98% or more; or reduce growth (e.g., growth rate or amount) of each of *Candida albicans*, *Candida krusei*, *Candida glabrata*, and *Candida tropicalis* by at least 90%, at least 95%, at least 96%, at least 97%, at least 98% or more.

A urogenital tract infection treated or prevented with the compositions or methods of the present disclosure may be associated with one or more of: menopause, *Lactobacillus* deficiency, chronic bacterial vaginosis, chronic yeast infection, chronic urinary tract infection, atrophic vaginitis, atrophic vaginosis, bacterial vaginosis in pregnancy, and vulva-vaginal candidiasis.

The compositions and methods disclosed herein can be particularly suitable for use in subjects for the treatment or prevention of asymptomatic or recurrent urogenital tract infection, including bacterial vaginosis, preterm delivery caused by bacterial vaginosis in pregnancy, *Lactobacillus* deficiency, chronic bacterial vaginosis, chronic yeast infection, chronic urogenital tract infection in menopause, atrophic vaginitis, atrophic vaginitis, vulva-vaginal candidiasis, and similar infections as abacterial vaginosis. Accordingly, in specific embodiments the subject has at least one symptom of the following conditions or is diagnosed with at least one of the following conditions: asymptomatic or recurrent urogenital tract infection, including bacterial vaginosis, preterm delivery caused by bacterial vaginosis in pregnancy, *Lactobacillus* deficiency, chronic bacterial vaginosis, chronic yeast infection, chronic urogenital tract infection in menopause, atrophic vaginitis, atrophic vaginitis, vulvavaginal candidiasis, and similar infections as abacterial vaginosis.

In some embodiments, administering the composition to the subject reduces, alleviates, or prevents a symptom, sign, or condition associated with the urogenital tract infection. Symptoms, signs, or conditions to be alleviated or prevented can include one or more of: pain or burning sensation while urinating or during intercourse; frequent urination; urge to urinate despite having an empty bladder; urine that is bloody, cloudy, or foul-smelling; pressure or cramping in groin, lower abdomen, or back; pain, irritation, or itching in urogenital area; redness, swelling, rash, or pain in vagina or vulva; vaginal discharge that is irregular, watery, thick, white, green, yellow, or foul-smelling; fever; and chills. Reduction and alleviation of the symptom can be determined by measuring the symptom using standard methods in the art and comparing the level of the symptom prior to administration of an effective amount of the Lr3613 and/or Lr3613-1 bacterial composition and after administration of an effective amount of the Lr3613 and/or Lr3613-1 bacterial composition. In specific embodiments, the symptom is reduced by about 10-100%, 20-100%, 30-100%, 40-100%, 50-100%, 60-100%, 70-100%, 80-100%, 20-90%, 30-90%, 40-90%, 50-90%, 60-90%, or 70-90% (e.g., by about 10-20%, 20-30%, 30-40%, 40-50%, 50-60%, 60-70%, 70-80%, 80-90%, or 90-100%), e.g., by about 10%, 15%, 20%, 25%, 30%, 35%, 40%, 45%, 50%, 55%, 60%, 65%, 70%, 75%, 80%, 85%, 90%, 95%, or 100%, or by at least 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% relative to the symptom prior to administration of the Lr3613 and/or Lr3613-1 bacterial composition.

G. Combination Therapies

In some embodiments, a bacterial composition disclosed herein is administered in combination with a second therapy (e.g., one or more additional therapies) known to be effective in treating infection, including urogenital infection in a subject or an associated symptom, sign, or condition. The composition may be administered before, after, or concurrent with the second therapy. In some embodiments, the composition is administered before the second therapy. In some embodiments, the composition is administered after the second therapy. In some embodiments, the composition is administered concurrent with the second therapy.

The second therapy may be an additional therapeutic agent, such as an antibiotic. The composition and the additional therapeutic agent can be administered in combination in the same composition or the additional therapeutic agent can be administered as part of a separate composition. In some embodiments, the second therapy is a non-composition therapeutic agent that is effective to treat the disorder or symptoms of the disorder. Any therapy for urinary tract infection, genital tract infection, or candidiasis known and practiced in the art, including those described in the present disclosure, can be combined as a second therapy with the administration of the bacterial composition of the present disclosure.

Exemplary combination therapies include, but are not limited to: administration of antibiotics, administration of antifungal medication, administration of dietary supplement (e.g., cranberry juice), vaginal estrogen therapy, and hydration. In some embodiments, the additional therapeutic agent comprises metronidazole, tinidazole, clindamycin, trimethoprim/sulfamethoxazole (e.g., Bactrim, Septra), fosfomycin (e.g., Monurol), nitrofurantoin (e.g., Macrodantin, Macrobid), Cephalexin (e.g., Keflex), Ceftriaxone. A composition disclosed in the present invention may be administered in combination with any of these therapies or agents.

V. Methods of Reducing Pathogenic Microbes

The present disclosure provides a method of reducing growth of a pathogenic microbe, comprising administering a composition comprising an amount of *Lactobacillus reuteri* 3613, *Lactobacillus reuteri* 3613-1, and/or an active variant thereof (i.e., a Lr3613 and/or Lr3613-1 bacterial composition). In some embodiments, the method comprises administering the composition to a subject, thereby reducing growth of a pathogenic microbe in a urogenital tract or in other sites of the body of the subject.

Lr3613, Lr3613-1, an active variant thereof, or a combination of any thereof can be administered at a dose of, for example, from about $1\times10^3$ to about $1\times10^{14}$ CFU, alternatively from about $1\times10^6$ to about $1\times10^{14}$ CFU, from about $1\times10^7$ to about $1\times10^{14}$ CFU, from about $1\times10^9$ to about $1\times10^{12}$ CFU, from about $1\times10^{10}$ to about $1\times10^{12}$ CFU, from about $1\times10^{11}$ to about $1\times10^{12}$ CFU, from about $1\times10^8$ CFU to about $1\times10^{11}$ CFU, or from about $1\times10^9$ CFU to about $1\times10^{10}$ CFU per day. In specific embodiments, the Lr3613 and/or Lr3613-1 bacterial composition can be administered at a dose of about $5\times10^9$ CFU per day.

The Lr3613 and/or Lr3613-1 bacterial composition can be administered daily, every other day, every two days, or as often as desired to reduce or alleviate symptoms disclosed herein. The Lr3613 and/or Lr3613-1 bacterial composition can be administered in a single unit dose administered at any time during a day. Alternatively, the composition can be administered in two or more doses administered at a single time of day or at two or more separate times of day. In some specific embodiments, the composition is administered once daily. In some embodiments, the composition is administered once daily for a period of 2 days, 3 days, 4 days, 5 days, 7 days, 1 to 5 days, 1 to 10 days, 1 to 120 days, 2 to 5 days, 2 to 10 days, 2 to 120 days, 10 days to 120 days, and for about 2 days, 5 days, 7 days, 10 days, 15 days, 30 days, or for 60 days.

Lr3613 and/or Lr3613-1 bacterial compositions as disclosed herein can be viable or non-viable when administered and/or when reaching the desired site of administration. Lr3613 bacterial composition disclosed herein can be administered together as a blend or mixture in a single dosage form, or can be administered in separate dosage forms at separate times.

In some embodiments, a reduction of pathogenic microbe growth in the present disclosure comprises a reduction of the growth rate or absolute numbers of the microbe, following administration of the Lr3613 and/or Lr3613-1 bacterial composition. For example, the growth rate of the pathogen can be reduced by about 10-100%, 20-100%, 30-100%, 40-100%, 50-100%, 60-100%, 70-100%, 80-100%, 20-90%, 30-90%, 40-90%, 50-90%, 60-90%, or 70-90% (e.g., by about 10-20%, 20-30%, 30-40%, 40-50%, 50-60%, 60-70%, 70-80%, 80-90%, or 90-100%), e.g., by about 10%, 15%, 20%, 25%, 30%, 35%, 40%, 45%, 50%, 55%, 60%, 65%, 70%, 75%, 80%, 85%, 90%, 95%, or 100%, or by at least 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% relative to the rate prior to administration of the Lr3613 and/or Lr3613-1 bacterial composition. Growth rate can be measured by standard methods known in the art, e.g., by analyzing data obtained by real time PCR, turbidimetry, or a hemocytometer. Similarly, the amount (e.g., absolute number) of the pathogen can be reduced following administration of the Lr3613 and/or Lr3613-1 bacterial composition. For example, the amount of the pathogen can be reduced by about 10-100%, 20-100%, 30-100%, 40-100%, 50-100%, 60-100%, 70-100%, 80-100%, 20-90%, 30-90%, 40-90%, 50-90%, 60-90%, or 70-90% (e.g., by about 10-20%, 20-30%, 30-40%, 40-50%, 50-60%, 60-70%, 70-80%, 80-90%, or 90-100%), e.g., by about 10%, 15%, 20%, 25%, 30%, 35%, 40%, 45%, 50%, 55%, 60%, 65%, 70%, 75%, 80%, 85%, 90%, 95%, or 100%, or by at least 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% relative to the amount prior to administration of the Lr3613 and/or Lr3613-1 bacterial composition. The amount of the pathogen can be measured by standard methods known in the art, e.g., by analyzing data obtained by real time PCR, turbidimetry, or a hemocytometer.

The methods disclosed herein can reduce the population or growth rate of a pathogen disclosed herein including but not limited to a Gram-negative bacterium, a Gram-positive bacterium, a Gram-variable bacterium, or a fungus. In specific embodiments, the pathogen may be one or more of *Escherichia coli, Gardnerella vaginalis,* and a *Candida* species (e.g., *Candida albicans, Candida krusei, Candida glabrata,* and *Candida tropicalis*).

The methods of the present invention may reduce the population of *Escherichia coli* by at least 97%; reduce the population of *Gardnerella vaginalis* by at least 93%; reduce the population of a *Candida* species by 98% or more; or reduce growth of each of *Candida albicans, Candida krusei, Candida glabrata,* and *Candida tropicalis* by 98% or more.

The growth inhibitory effects of the compositions and methods against potential pathogens in the urogenital tract and in the body, disclosed in the present disclosure, can be attributed to the metabolic activity of the Lr3613 strain, Lr3613-1 strain, and/or their active variant strain, generating multiple distinct inhibitory metabolites. The composition of the present disclosure exerts its inhibitory effects against potential pathogens through at least three modes of action discussed above. Briefly, these modes of action can include: (a) production of reuterin; (b) production of hydrogen peroxide; and (c) production of lactic acid and regulation or reduction of pH. The composition of the present disclosure may be capable of acting through at least one or all of these three mechanisms of action simultaneously to treat a subject for infection, including urogenital infection.

VI. Kits and Products

Kits for performing any of the methods of the invention are provided herein. Such kits include one or more Lr3613 and/or Lr3613-1 bacterial composition(s) of the present invention, and instructions for use, e.g., instructions for administering a prophylactically or therapeutically effective amount of a composition comprising Lr3613, Lr3613-1, and/or an active variant thereof.

Further embodiments of the present invention are represented by a product, which comprises one or composition(s) of the present invention. The products can be pharmaceutical products, suppositories, dairy products, drinks, nutritional supplements, food products, and/or nutrition feeds. Dairy products of the present invention can include milk, yogurt, cheese, homogenized products (based on milk, cheese, fruit), fermented or non-fermented milk (including powdered milk, non-lactose containing milk, milk shakes) containing probiotics. Therapeutic cheese can be obtained by the addition of suitable probiotic microorganisms in a concentrated dried form in a certain processing phase of the cheese in order to guarantee the supply of the dose of the microorganisms necessary for the organism. The drinks can be instantaneous drinks or water containing the compositions according to the present invention. Said integrators, dairy and food products are particularly suitable for use in the treatment or prevention of asymptomatic, symptomatic, or recurrent urogenital tract infection.

EXAMPLES

This invention is further illustrated by the following examples which should not be construed as limiting. The entire contents of all references, patents and published patent applications cited throughout this application, as well as the informal Sequence Listing and Figures, are hereby incorporated herein by reference.

Example 1: Strain Identity and Antibiotic Resistance of *Lactobacillus reuteri* 3613 (Lr3613)

Experimental Methods
Antibiotic Resistance NARMS Panel Methods

*Lactobacillus reuteri* 3613 was picked into 10 mL of MRS broth and grown overnight at 37° C. At 24 hours, the isolate was transferred into a 15 mL conical tube and centrifuged at 4700 rpm for 10 min. A sterile swab was used to acquire a portion of the bacterial pellet, which was resuspended in sterile ddH$_2$O tubes. The density of bacteria was compared against a 0.5 McFarland standard to determine the optimal dilution. 15 microliters of the ddH$_2$O was transferred into the 5 mL tubes of Mueller-Hinton broth and the mixture was vortexed and poured into a sterile boat. As per the manufacturer's instructions, 50 microliters of bacterial suspension was added into each well of the NARMS plate and a plastic seal was placed over each plate. The plates were placed in an anaerobic box and placed at 37° C. overnight. The plates were removed at 41 hours and each well was assessed as either positive or negative depending on if there was any growth in the well.

Genome Sequencing

A draft genome was obtained for strains by assembling paired-end reads of genomic DNA. A shotgun genomic library was prepared with the Hyper Library construction kit (Kapa Biosystems, Wilmington, MA) with gDNA fragment sizes ranging from 300 to 1000 bp. A mate-pair library was constructed with the Nextera Mate Pair Library Sample Prep kit followed by the TruSeq DNA Sample Prep kit (Illumina, San Diego, CA). The libraries were pooled in equimolar concentration, quantified by qPCR and sequenced on one lane for 251 cycles from each end of the fragments on a HiSeq 2500 using a HiSeq Rapid SBS sequencing kit version 2 (Lp1037, Le 1E-1, Lc1854) or a MiSeq using MiSeq 600-cycle sequencing kit version 3 (Lr3613). Fastq files were generated and demultiplexed with the bcl2fastq v2.17.1.14 Conversion Software (Illumina, San Diego, CA). Paired reads were merged to generate longer single reads with PEAR 0.9.6 (Zhang et al., 2014). High quality reads that passed data preprocessing steps were assembled with SPAdes 3.5.0 assembler (Nurk et al., 2013). The mate-pair library was used to join assembled contigs. The assembled scaffolds were annotated using the prokka 1.11 annotation pipeline (Seemann, 2014).

A draft genome was obtained for *Lactobacillus reuteri* 3613 to compare to previously patented strains by assembling paired-end Illumina reads of genomic DNA. A shotgun genomic library was prepared with the library construction kit from Kapa Biosystems with an average gDNA fragment size of 550 bp (300-1000 bp). The library was sequenced on one MiSeq flowcell for 301 cycles using a MiSeq 600-cycle sequencing kit v3 (Illumina, San Diego, CA). Paired reads were uploaded to the Pathosystems Resource Integration Center (PATRIC), a BACTERIAL BIOINFORMATICS RESOURCE CENTER (https://www.patricbrc.org/) (Davis et al., 2016; Wattam et al., 2014). The reads were assembled using the auto assembly strategy that runs BayesHammer (Nikolenko et al., 2013) on short reads, followed by three assembly strategies that include Velvet (Zerbino and Birney, 2008), IDBA (Peng et al., 2010) and Spades (Bankevich et al., 2012), each of which is given an assembly score by ARAST, an in-house script. The best assembly, as selected by PATRIC, was then submitted to the Genome Annotation Service that uses the RAST tool kit (RASTtk) (Brettin et al., 2015) to annotate genomic features.

Results

Strain Identity

As assessed by a nearest neighbor genome analysis, the draft genome demonstrated highest similarity to *Lactobacillus reuteri* DSM 20016, the type strain of *Lactobacillus reuteri*, confirming its identity as member of the *Lactobacillus reuteri* species. Table 1 shows genetic characteristics of *Lactobacillus reuteri* 3613.

TABLE 1

General characteristics of *Lactobacillus reuteri* 3613 (Lr3613)

| Genome | Lr3613 |
|---|---|
| Size (Mb) | 2.3 |
| Contigs | 189 |
| Coverage | >224 |
| % GC | 38.5 |
| PATRIC submission | 1598.273 |
| CDS | 2419 |
| Hypothetical genes | 615 |
| CRISPR array | 2 |
| ribosomal RNA | 11 |
| Repeat region | 406 |
| ARDB | 1 |
| CARD | 1 |
| ResFinder 2.1 | 1 |
| Virulence Factors | 0 |

Antibiotic Resistance

The minimum inhibitory concentration (MIC) were determined for the following antibiotics: penicillin, tigecycline, daptomycin, tylosin tartrate, quinupistin, linezolid, nitrofurantoin, vancomycin, gentamycin, kanamycin, streptomycin, erythromycin, lincomycin, tetracycline, and chloramphenicol. As no standard method exists for the testing of antibiotic susceptibility in Lactobacilli, antibiotic susceptibility was carried out using the National Antibiotic Resistance Monitoring System (NARMS) testing plates at 24 hours.

There are no established sensitivity/resistance MIC levels for Lactobacilli in the US, therefore the accepted levels from the European Food Safety Authority were used. Lr3613 demonstrated intrinsic resistance to ciprofloxacin, tigecycline/vancomycin, and tetracycline.

Through genomic analysis, a lincosamide nucleotidyltransferase (1598.273.peg.1812) was detected in *L. reuteri* 3613. This gene was also one of the four resistance genes detected in *L. reuteri* 1E-1, a commercial competitor strain sequenced for comparative purposes. The functionality of the gene lnuA has not been confirmed. Lr3613 is susceptible to lincomycin at concentrations above 45 µg/ml, and it is no more resistant than other *Lactobacillus* strains tested.

Resistance to fluoroquinolones typically arises due to alterations in the target enzymes (DNA gyrase and topoisomerase IV), but may also be due to efflux of the compounds from the cells. It is not clear how resistance to fluoroquinolones is mediated in *Lactobacillus* strains, but no fluoroquinolone antibiotic resistance genes were detected in the draft genomes.

*L. reuteri* Lr3613 is resistant to the glycopeptides, but most lactobacilli are inherently resistant due to the lack of a cell wall target allowing these antibiotics to bind to the cell wall.

Lr3613 demonstrates resistance to tetracycline at 32 µg/mL, however there are no tetracyline resistance genes present and therefore this resistance is considered intrinsic and not associated with any mobile elements such as transposons and is therefore believed to be nontransferable.

Hemolysin and Toxin Production

There is no known hemolytic activity or potential eukaryotic toxin production of this *Lactobacillus reuteri* species.

GRAS and QPS Status

*L. reuteri* has been granted GRAS status by FDA and QPS status by EFSA. The species *Lactobacillus reuteri* is included in the EFSA-list of bacteria that are presumed to be safe and has been given GRAS-status by the FDA. *L. reuteri* is available through multiple probiotic products and without the report of adverse, short term reactions. There is no available evidence to consider the strain *L. reuteri* 3613 at the dosage of $10^9$-$10^{10}$ CFU/g to be unsafe.

The *L. reuteri* 3613 strain was deposited at NRRL and given the designation B-67262.

Example 2: Antimicrobial Activity of *Lactobacillus reuteri* 3613 (Lr3613) In Vitro 1) Antimicrobial Activity of *Lactobacillus reuteri* 3613 Against *Escherichia coli*

Experimental Methods

Inhibition studies were performed to test the effects of *Lactobacillus reuteri* 3613 on the potential to inhibit the growth of four *E. coli* strains, three isolated from the vaginal tract and one isolated from human stool. *L. reuteri* 3613 was grown overnight in MRS broth. Reuterin production was induced with the addition of glycerol. Overnight probiotic cultures were centrifuged and washed with sterile PBS three times. The pellet was resuspended in filter-sterilized 0.02% glycerol solution and incubated anaerobically at 32° C. for 2 hr. After incubation, the culture was centrifuged again, and the bacteriocin supernatant was filter sterilized. Briefly, 250 µl of the filter sterilized bacteriocin supernatant was diluted with 750 µl of sterile BHI broth, a 25% supernatant solution. In duplicate wells, 390 µl of the bacteriocin supernatant solution was added to a 48-well microtiter plate. The overnight *E. coli* cultures were diluted 1:5 in sterile BHI broth and 10 µl of diluted culture was added to each well. Sterile BHI broth was inoculated with the respective *Candida* species as a positive control and uninoculated sterile BHI broth was used as a negative control. All experiments were completed in triplicate.

Results

FIG. 1 provides growth inhibition of vaginal and stool *Escherichia coli* isolates by *Lactobacillus reuteri* strain-conditioned bacteriocin supernatant (n=3). Overall, *L. reuteri* 3613 bacteriocin supernatant demonstrated an ability to inhibit the growth of all four *E. coli* strains. The effectiveness of reuterin inhibiting the growth of the *E. coli* strains is indicated by a greater than 97% reduction of growth of all four isolates. The results demonstrate that *L. reuteri* 3613 is effective at preventing the growth of vaginal and stool associated isolates that could have the potential of causing a urinary tract infection.

2) Antimicrobial Activity of *Lactobacillus reuteri* 3613 Against *Gardnerella vaginalis*

Experimental Methods

Inhibition studies of *G. vaginalis* compared the effect of *L. reuteri* 3613 and a competitor *L. reuteri*. Both probiotic strains were grown overnight in MRS broth, which was filter sterilized to remove bacterial cells. Briefly, 250 µl of the overnight filter sterilized supernatant was diluted with 750 µl of sterile NYC III broth, a 25% supernatant solution. In duplicate, 390 µl of the supernatant solution were added to a 48-well microtiter plate. The overnight *G. vaginalis* culture was diluted 1:5 in sterile NYC III broth and 10 µl of diluted culture was added to each well. Sterile NYC III broth was inoculated with *G. vaginalis* as a positive control and un-inoculated sterile NYC III broth was used as a negative control. To account for the effects of pH on pathogen reduction, an aliquot of the overnight filter-sterilized supernatant was brought to neutral MRS (pH of 6.2) using 1M NaOH. The neutralized supernatant was then used to set up the inhibition assay as described above. Neither pH neutralized probiotic culture was effective at inhibiting *G. vaginalis* growth. In a third assay, production of the bacteriocin-like molecule reuterin was induced with the addition of glycerol to the probiotic medium. Overnight probiotic cultures were centrifuged and the bacterial pellet was washed with sterile PBS three times. The pellet was resuspended in filter-sterilized 0.02% glycerol solution and incubated anaerobically at 32° C. for 2 hr. After incubation, the culture was centrifuged again, and the bacteriocin supernatant was filter sterilized and used to set up the inhibition assay as described above.

Results

Figure 2:
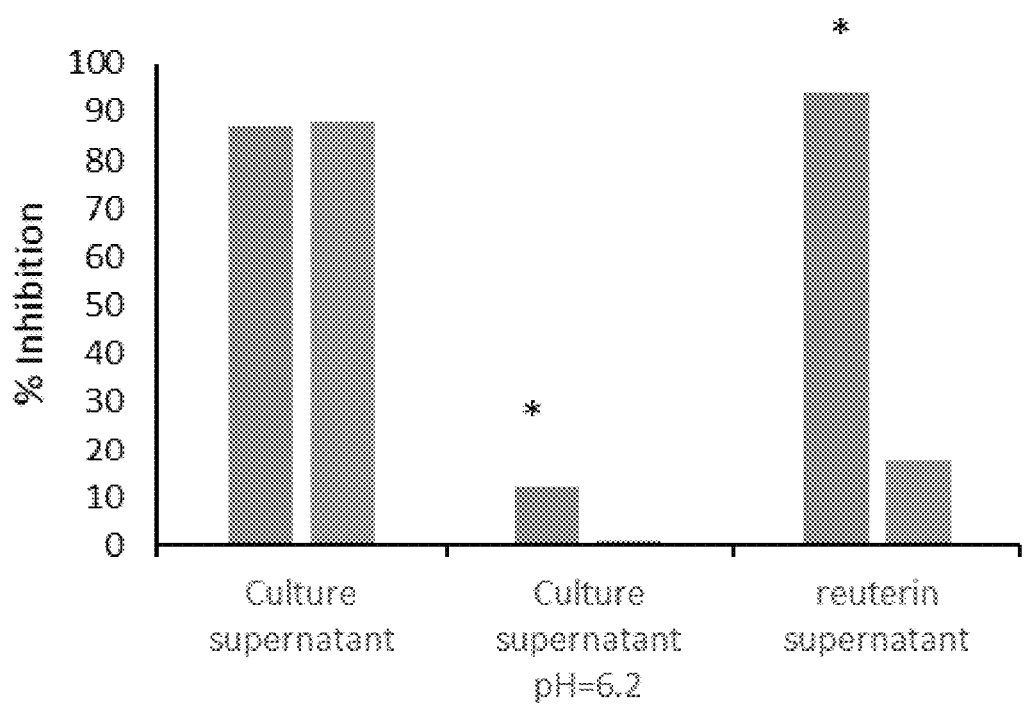
FIG. 2 shows growth inhibition of *Gardnerella vaginalis* by: 1) a culture supernatant of *Lactobacillus reuteri* 3613 or a *Lactobacillus reuteri* competitor strain cultured in MRS broth; 2) supernatant of 1), which was subsequently neutralized (to pH of 6.2); and 3) culture supernatant of *Lactobacillus reuteri* 3613 or a *Lactobacillus reuteri* competitor strain cultured in MRS broth, and then incubated anaerobically in 0.02% glycerol solution to induce production of reuterin. **indicates $p \leq 0.0007$.

FIG. 2 provides inhibition of *Gardnerella vaginalis* by *L. reuteri* 3613 and *L. reuteri* (competitor) MRS supernatant, neutralized MRS supernatant, and Lr3613/reuterin supernatant (p≤0.05). After 24-hour incubation, both probiotic supernatants demonstrated significant reduction in *G. vaginalis* growth. However, once probiotic MRS supernatants were neutralized to a pH of 6.2 neither were effective. Probiotic cultures grown in the presence of glycerol were effective in decreasing *G. vaginalis* growth.

Overall, *L. reuteri* 3613 demonstrated a superior ability to inhibit the growth of *G. vaginalis* in vitro. Inhibition with the MRS supernatant showed a 93% reduction in *G. vaginalis* growth for both *L. reuteri* isolates indicating that the likely production of lactic acid leading to a reduction in pH (pH=4.2) is effective at limiting bacterial growth. When the pH was brought back to neutral MRS broth (pH=6.2), the supernatant was ineffective for both *L. reuteri* isolates at inhibiting *G. vaginalis* growth at greater than 20%. Reuterin was detected by HPLC in the 3613 strain however reuterin was absent in the competitor strain. When grown under conditions to produce reuterin, *L. reuteri* 3613, the conditioned medium inhibited *G. vaginalis* growth by over 90%. The results demonstrate that *L. reuteri* 3613 demonstrate the ability to reduce *G. vaginalis* growth by acid production, as well as bacteriocin production demonstrating possible treatment or prevention options for bacterial vaginosis.

3) Antimicrobial Activity of *Lactobacillus reuteri* 3613 Against *Candida albicans*

Experimental Methods

Inhibition studies of *C. albicans* compared the effect of *L. reuteri* 3613 a competitor strain. Both probiotic strains were grown overnight in MRS broth, which was filter sterilized to remove bacterial cells.

Briefly, 250 µl of the overnight filter sterilized supernatant was diluted with 750 µl of sterile MRS broth, a 25% supernatant solution. In duplicate, 390 µl of the supernatant solution was added to a 48-well microtiter plate. The overnight *C. albicans* culture was diluted 1:5 in sterile MRS broth and 10 µl of diluted culture was added to each well. Sterile MRS broth was inoculated with *C. albicans* as a positive control and inoculated sterile MRS broth was used as a negative control.

An aliquot of the overnight filter-sterilized supernatant was brought up to a neutral MRS pH of 6.2. The neutralized supernatant was then used to set up the inhibition assay as described above.

Reuterin production was induced with the addition of glycerol. Overnight probiotic cultures were centrifuged and washed with sterile PBS three times. The pellet was resuspended in filter-sterilized 0.02% glycerol solution and incubated anaerobically at 32° C. for 2 hr. After incubation, the culture was centrifuged again, and the bacteriocin supernatant was filter sterilized and used to set up the inhibition assay as described above.

Results

Figure 3:
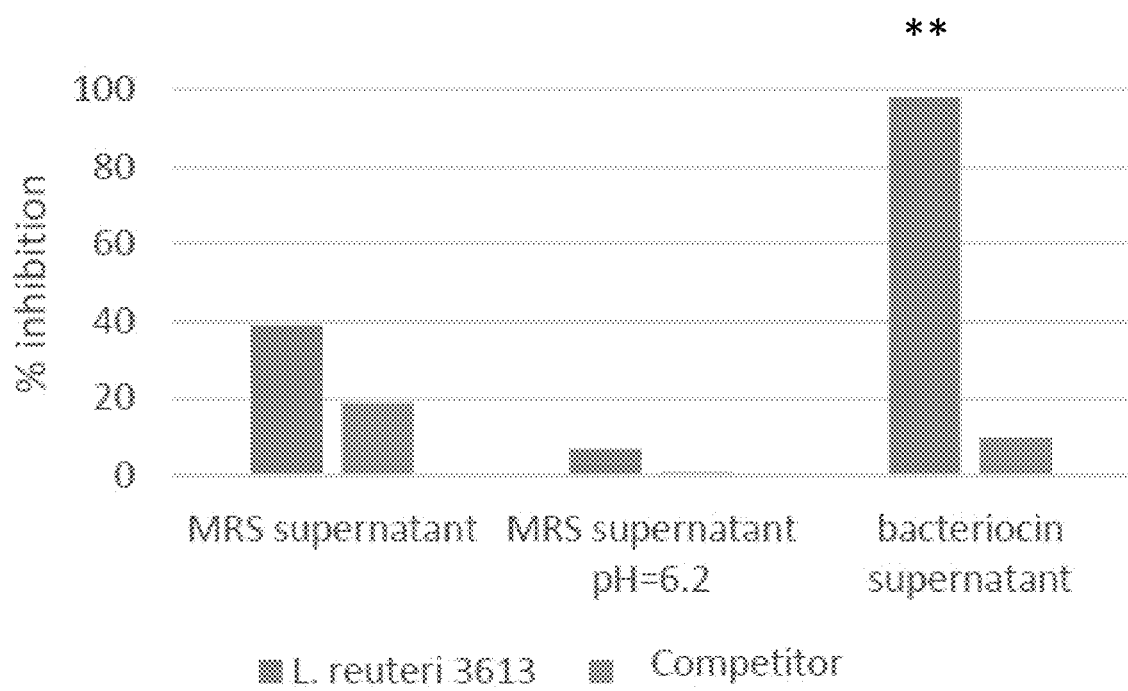
FIG. 3 demonstrates growth inhibition of *Candida albicans* by: 1) culture supernatant of *Lactobacillus reuteri* Lr3613 or a *Lactobacillus reuteri* competitor strain cultured in MRS broth; 2) supernatant of 1), which was subsequently neutralized (to pH of 6.2); and 3) *Lactobacillus reuteri* Lr3613 or a *Lactobacillus reuteri* competitor strain-conditioned bacteriocin supernatant (culture supernatant of the respective bacteria cultured in MRS broth, and then incubated anaerobically in 0.02% glycerol solution to induce production of reuterin). *indicates $p \leq 0.05$.
Figure 4:
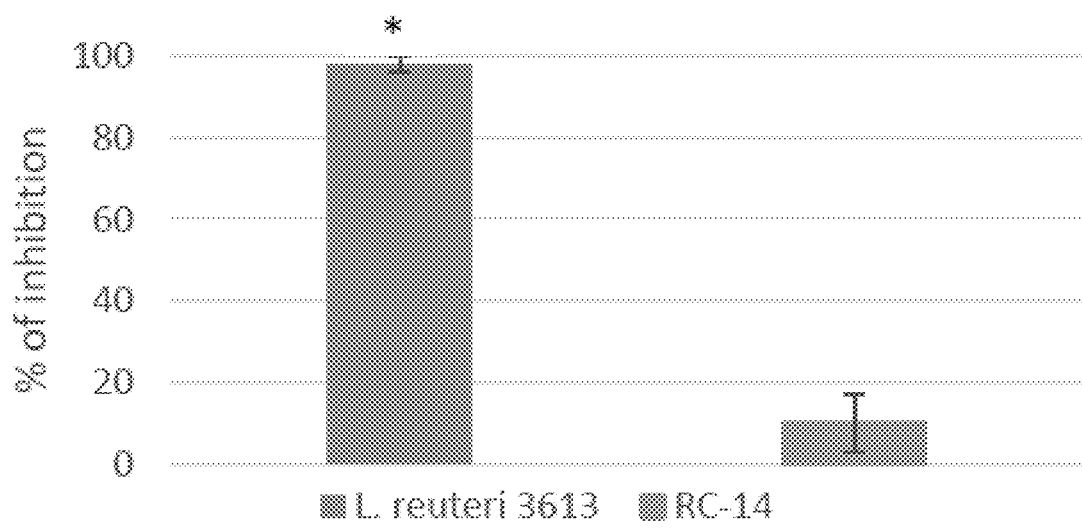
FIG. 4 shows growth inhibition of *Candida albicans* by *Lactobacillus reuteri* 3613 or a *Lactobacillus reuteri* competitor strain RC-14-conditioned bacteriocin supernatant (i.e., culture supernatant of the respective bacteria cultured in YPD broth, and then incubated anaerobically in 0.02% glycerol solution to induce production of reuterin). (n=3; $p \leq 0.05$).
Figure 5:
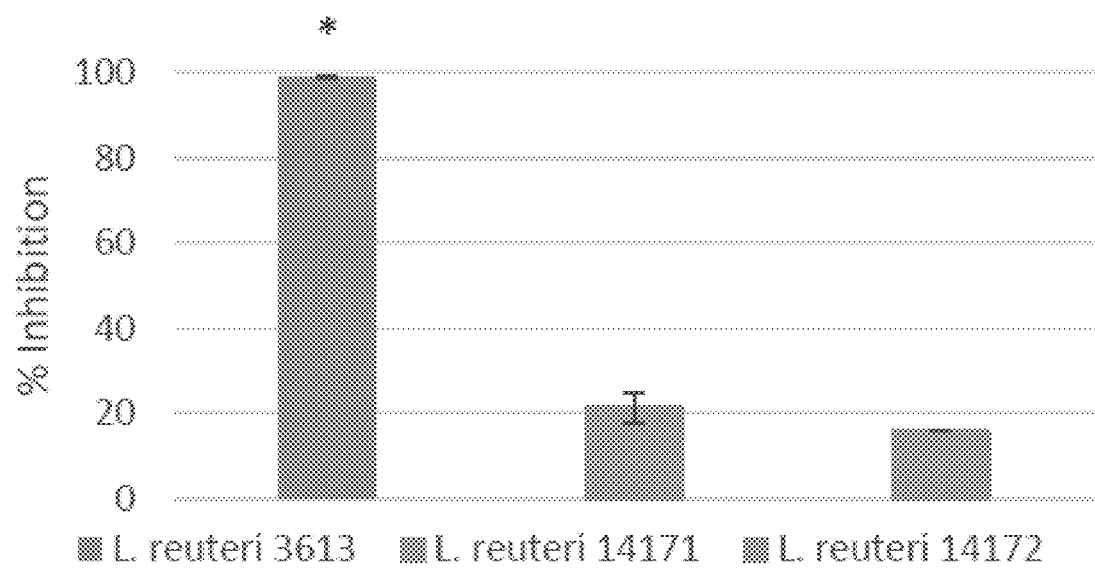
FIG. 5 demonstrates inhibition of *Candida krusei* by *Lactobacillus reuteri* strains 3613, 14171, or 14172-conditioned bacteriocin supernatant (i.e., culture supernatant of the respective bacteria cultured in YPD broth, and then incubated anaerobically in 0.02% glycerol solution to induce production of reuterin). (n=3; $p \leq 0.05$).
Figure 6:
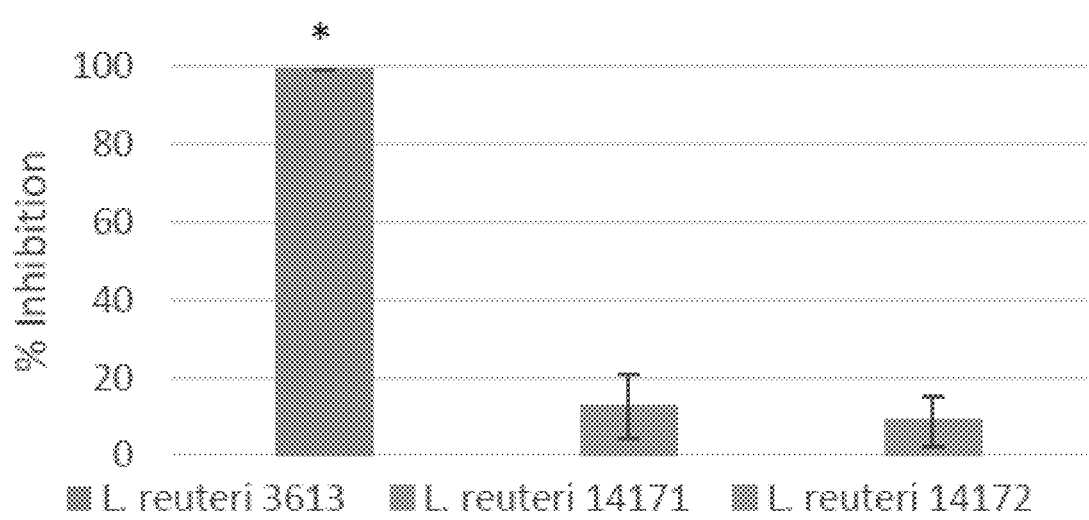
FIG. 6 shows inhibition of *Candida glabrata* by *Lactobacillus reuteri* strains 3613, 14171, or 14172-conditioned bacteriocin supernatant (i.e., culture supernatant of the respective bacteria cultured in YPD broth, and then incubated anaerobically in 0.02% glycerol solution to induce production of reuterin). (n=3; $p \leq 0.05$).
Figure 7:
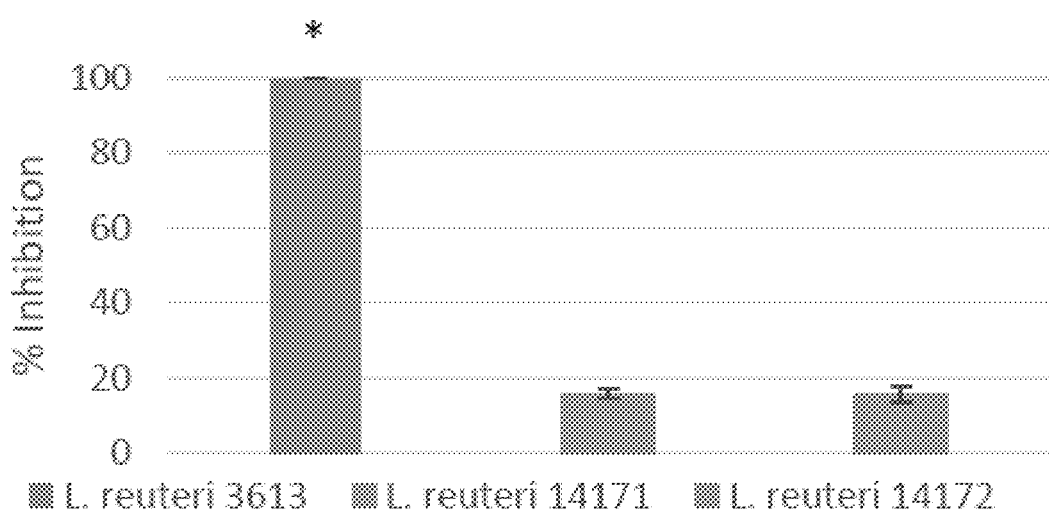
FIG. 7 shows inhibition of *Candida tropicalis* by *Lactobacillus reuteri* strains 3613, 14171, or 14172-conditioned bacteriocin supernatant (i.e., culture supernatant of the respective bacteria cultured in YPD broth, and then incubated anaerobically in 0.02% glycerol solution to induce production of reuterin). (n=3; $p \leq 0.05$).

FIG. 3 provides inhibition of *Candida albicans* by *L. reuteri* 3613 and Competitor strain in MRS supernatant, neutralized MRS supernatant, and bacteriocin supernatant. Overall, both *L. reuteri* strains demonstrated an ability to inhibit the growth of *C. albicans* in vitro, but *L. reuteri* 3613 showed an increased ability compared to that of the competitor strain. Inhibition with the MRS supernatant showed a 40% reduction in *C. albicans* growth indicating that the production of lactic acid leading to a reduction in pH (pH=4.2) is effective at limiting fungal growth. When the pH was brought back up to neutral MRS broth (pH=6.2), the supernatant was much less effective, only about 8% inhibition. The competitor strain does not have the ability to produce the effective bacteriocin like compound, which is demonstrated by the difference in growth reduction with the bacteriocin supernatant. The effectiveness of reuterin inhibiting the growth of *C. albicans* is indicated by a 98% reduction of growth by *L. reuteri* 3613 compared to a 10% reduction in growth by the competitor strain. The bacteriocin supernatant percent inhibition was statistically different (p≤0.0007) between *L. reuteri* 3613 and the competitor. The results demonstrate that *L. reuteri* 3613 outperformed the competitor in the reduction of *C. albicans*.

4) Antimicrobial Activity of *Lactobacillus reuteri* 3613 Against *Candida* Species Experimental Methods Inhibition studies were run to test the effects of *Lactobacillus reuteri* 3613 to inhibit the growth of four *Candida* species. *L. reuteri* 3613 and competitor *Lactobacillus reuteri* (RC-14, *L. reuteri* 14171, and *L. reuteri* 14172) were grown overnight in MRS broth. Reuterin production was induced with the addition of glycerol. Overnight probiotic cultures were centrifuged and washed with sterile PBS three times. The pellet was resuspended in filter-sterilized 0.02% glycerol solution and incubated anaerobically at 32° C. for 2 hr. After incubation, the culture was centrifuged again, and the bacteriocin supernatant was filter sterilized.

Briefly, 250 µl of the filter sterilized bacteriocin supernatant was diluted with 750 µl of sterile YPD broth, a 25% supernatant solution. In duplicate wells, 390 µl of the bacteriocin supernatant solution was added to a 48-well microtiter plate. The overnight *Candida* cultures were diluted 1:5 in sterile YPD broth and 10 µl of diluted culture was added to each well. Sterile YPD broth was inoculated with the respective *Candida* species as a positive control and uninoculated sterile YPD broth was used as a negative control. All experiments were completed in triplicate.

Results

FIGS. 4-7 show growth inhibition of *Candida albicans*, *Candida krusei*, *Candida glabrata*, and *Candida tropicalis*, respectively, by Lr3613 and its competitor strains-conditioned bacteriocin (n=3; p≤0.05). Overall, *L. reuteri* 3613 bacteriocin supernatant demonstrated an ability to inhibit the growth of all four *Candida* species in vitro significantly better than the competitor strains. The competitor strains do not have the ability to produce reuterin, which is demonstrated by the difference in growth reduction with the bacteriocin supernatant. The effectiveness of reuterin inhibiting the growth of *Candida* species is indicated by a greater than 98% reduction of growth in all four *Candida* species. The results demonstrate that *L. reuteri* 3613 outperforms the competitor *Lactobacillus reuteri* strains.

Example 3: Effect of *Lactobacillus reuteri* 3613 in Controlling Urinary Tract Infection in Humans Experimental Methods Two college-aged females were plagued with recurring urinary tract infections. After repeatedly seeking antibiotic treatments to rectify past outbreaks, each sought other methods to prevent onset of urinary tract infections (UTI). Following a period, not less than 30 days, without antibiotic treatment the subjects used a swab to sample the vaginal microbial constituents. These samples were assessed for the presence of Lr3613 by using strain specific PCR primers. After initial sampling each subject began taking a Lr3613 ($5 \times 10^9$ CFU per dose) by mouth once daily for 60 days. After 30 and 60 days, the vaginal swab was again used to assess the presence of Lr3613. The frequency of UTI were assessed during this 60-day period.

Results

Figure 8A:
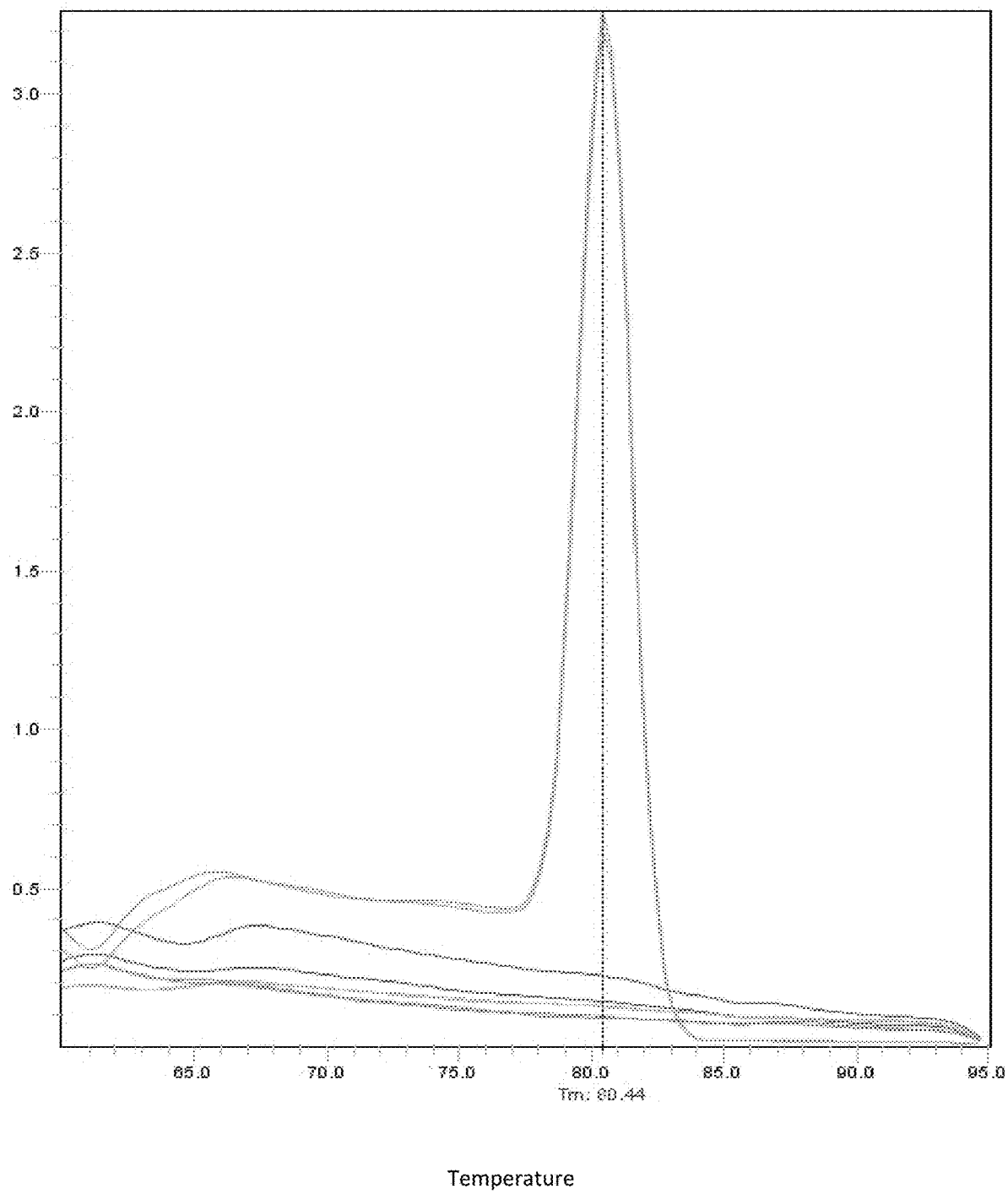
FIG. 8A provides a day 0 melt curve and melting temperatures of PCR fragments of *Lactobacillus reuteri* 3613 demonstrating only the positive control was amplified.
Figure 8B:
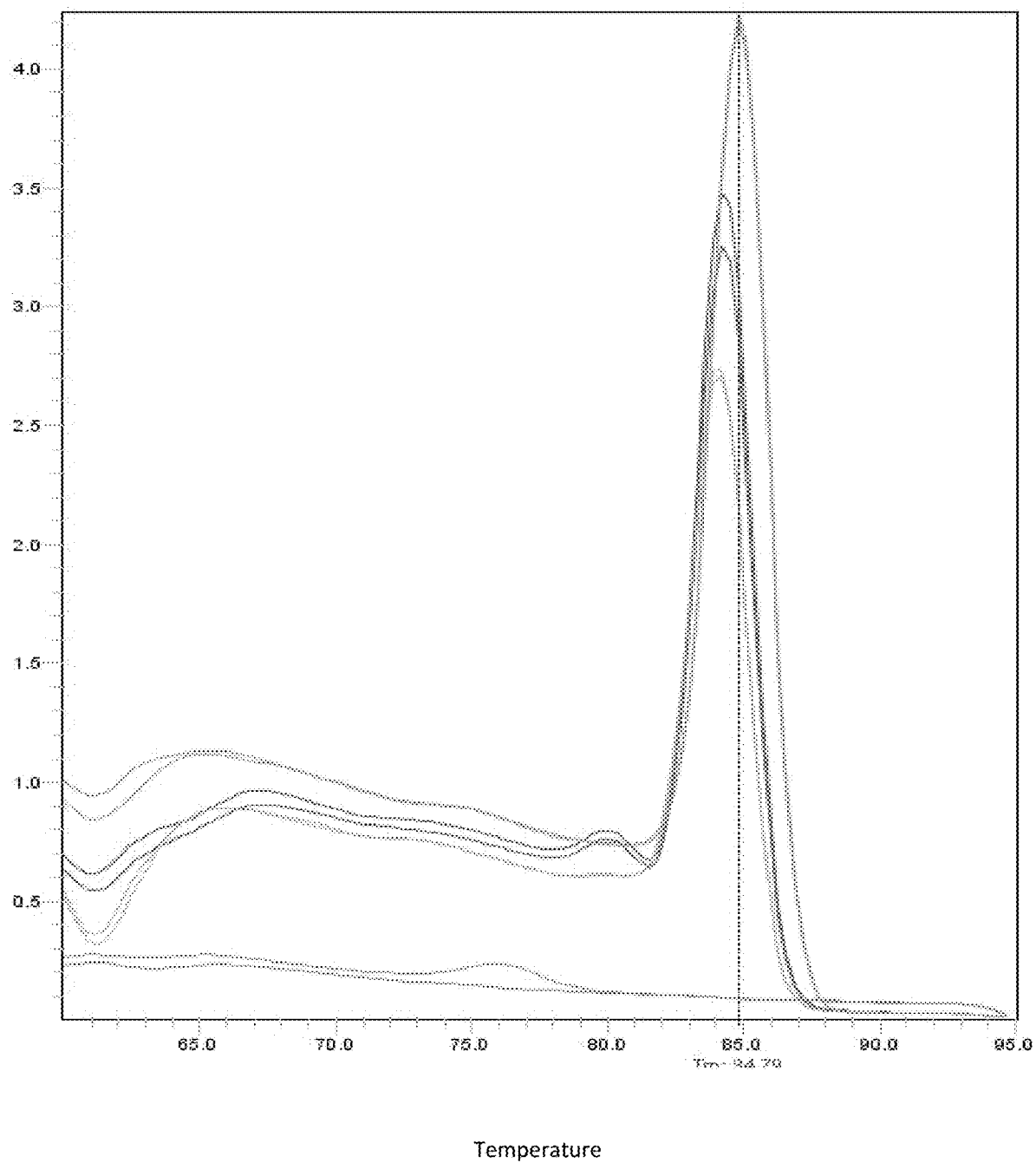
FIG. 8B provides a day 30 melt curve and melting temperatures of PCR fragments of *Lactobacillus reuteri* 3613 demonstrating a single melting temperature and amplification of products for the positive control and vaginal swabs.

FIGS. 8A and 8B provide a melt curve and melting temperatures of PCR fragments of Lr3613 on day 0 and 30, respectively. Tables 2 and 3 provide melting temperatures of PCR fragments of Lr3613 on day 0 and 30, respectively. At the time of initial sampling (day 0), no Lr3613 was detected in the vaginal swabs (FIG. 8A) by PCR amplification and melt curve analysis. However, after 30 days of probiotic treatment both subjects demonstrated Lr3613 in the urogenital tract (FIG. 8B), Lr3613 was also present at 60 days (not shown). During the probiotic treatment, no UTI were detected by subject reporting. The results demonstrate that oral administration of Lr3613 survives passage through the gastrointestinal tract and Lr3613 is able to access and potentially populate the vagina, preventing the onset of UTIs.

TABLE 2

Melting temperatures of PCR fragments of Lr3613 on day 0

| Day 0 | Tm |
| --- | --- |
| Neg | 61.112 |
| Pos | 80.438 |

TABLE 2-continued

Melting temperatures of PCR fragments of Lr3613 on day 0

| Day 0 | Tm |
| --- | --- |
| Swab 14 | 64.222 |
| Swab 80 | 66.665 |

TABLE 3

Melting temperatures of PCR fragments of Lr3613 on day 30

| Day 30 | Tm |
| --- | --- |
| Neg | 61.198 |
| Pos | 80.685 |
| Swab 14 | 80.461 |
| Swab 80 | 80.536 |

Example 4: Development of *Lactobacillus reuteri* 3613-1 (Lr3613-1) Strain

The parent strain, *L. reuteri* 3613 exhibited resistance to the antibiotic lincomycin, as provided in Example 1. Genetic interrogation of the genome and all associated plasmids of *L. reuteri* 3613 revealed the lnuA gene, responsible for lincosamide resistance, was encoded on an extrachromosomal plasmid. It was determined that none of the genes on the plasmid were involved in the beneficial functionality of the microbe and removal of the plasmid would have no impact on strain functionality. The plasmid in *L. reuteri* 3613 was cured by protoplast formation using a method similar to one used by Roos and Rolander (Rosander et al., 2008) to produce *L. reuteri* DSM 17938 (GRN 410), a GRAS strain free of lincosamide antibiotic resistance. Protoplast formation was the chosen method of plasmid curing as it is a natural process and not a biotechnological technique (Vescovo et al., 1984). Protoplast formation removes the cell wall and nutritionally starves the cell, leading to cellular stress and spontaneous loss of unneeded plasmids. Cells then slowly recover on sucrose plates and colonies can be picked and grown individually on MRS plates both with and without lincomycin.

Using this approach, 5,088 isolates were picked and examined by PCR for lnuA gene. All candidate colonies that tested negative for lnuA by PCR were plated on MRS plates with and without lincomycin to determine any false candidates. False positive candidates can arise as a result of variable DNA concentrations and quality. Of these isolates only 3 isolates failed to grow on MRS plates with lincomycin. One colony in particular grew well on antibiotic free MRS plates but did not grow at all on MRS plates with lincomycin. This colony was replated and assumed to be a true candidate isolate that had lost the lnuA gene.

The lincomycin sensitive candidate was then further examined by PCR for the lnuA gene, and plasmid specific markers (zinc ribbon gene and XRE family transcriptional regulator) by multiple PCR reactions. Finally, the strain was subjected to whole-genome sequencing using both lumina and minion to demonstrate deletion of the plasmid and stability of the chromosomal genome.

Figure 9:
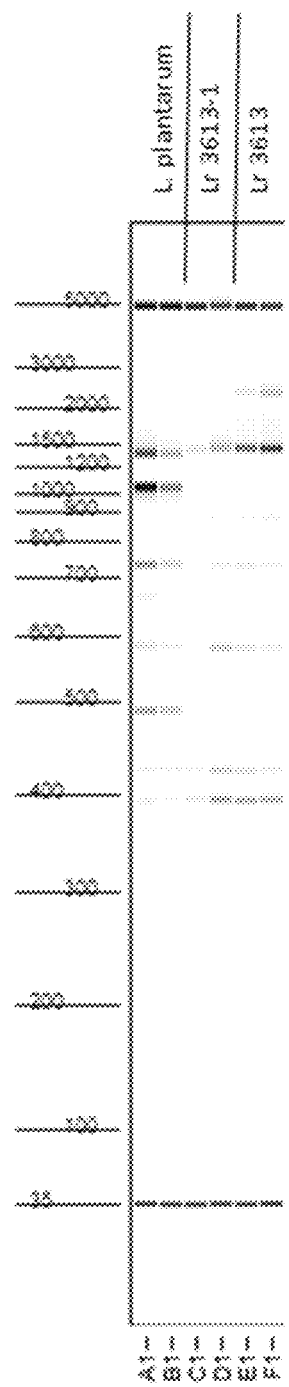
FIG. 9 shows results of random amplified polymorphic DNA (RAPD) analysis of *Lactobacillus reuteri* strain 3613-1 (Lr3613-1), *Lactobacillus reuteri* strain 3613 (Lr3613), and an unrelated Lactiplantibacillus *plantarum* strain.

The parent and daughter strain were then compared using RAPD PCR and demonstrated a pattern identical to each other using the selected primers (FIG. 9). As shown in FIG. 9, the banding pattern of the daughter strain was consistent with that of the parent strain Lr3613, and both *L. reuteri* strains exhibited a different banding pattern from *L. plantarum*, demonstrating that the daughter strain is not a contaminant but a variant strain closely related to the parent strain of *L. reuteri* 3613. The result also shows that the removal of the plasmid and protoplast formation protocol does not impact the chromosomal genome. The daughter strain has been assigned the strain number 3613-1.

The deletion of the lincomycin resistance in Lr3613-1 was confirmed by the minimum inhibitory concentration (MIC) of lincomycin for the parent and daughter strains. The MIC were found to be >8 µg/ml in the parent strain Lr3613, and 1 µg/ml in Lr3613-1, which was the lowest value tested. A complete NARMS panel was run to assess any antibiotic resistance of the strain.

In sum, the cured strain Lr3613-1 was identical to the parent strain Lr3613 except for the absence of the plasmid encoding the lnuA gene. The Lr3613-1 strain was deposited at NRRL and given the designation B-68035. The daughter strain is substantially equivalent to the parent strain and evidence demonstrating the safety of *L. reuteri* 3613 is equally applicable to strain 3613-1.

Example 5: Biochemical Analysis of *Lactobacillus reuteri* 3613-1 (Lr3613-1) Strain Using Analytical Profile Index (API) Strip Experimental Materials and Methods
Analytical Profile Index (API) Strip The API strip (Biomerieux, Durham, NC; item ID 50300) classifies bacteria based on biochemical tests, largely on the ability of the bacteria to utilize different carbon sources. The strip contains wells of dried substrates that are resuspended in bacterial culture. The color of the well post-incubation determines the ability of the bacteria to break down or metabolically utilize the substance.
Preparation of Bacteria An overnight culture of Lr3613-1 was pelleted at 10,000×g for 10 min at room temperature. The supernatant was decanted, and the pellet was washed with 10 ml sterile peptone and centrifuged as above. The supernatant was again decanted, and the pellet was resuspended in 1 ml sterile peptone. Drop by drop, the resuspended pellet was inoculated into a sterile 10 ml peptone tube until it reached a McFarland of 2.0. Using the 2.0 McFarland tube, two times the number of drops from the previous step were used to inoculate an ampule of API 50 CHL Medium (Biomerieux). The suspension was then vortexed and used immediately for analysis using the API strip.
Inoculation of API Strip The bottom half of each capule was inoculated with approximately 250 µl of the API 50 CHL bacterial suspension making sure not to fill the top half of the capule. All test wells were covered with mineral oil and incubated anaerobically for 48 hours at 37° C.
Interpretation of the Strip After 48 hours of incubation, the color changes were recorded on the provided results sheet. A positive test result was noted if the bottom half of the capule was yellow, indicating a pH change. A negative test result was recorded if the capule remained purple. Capule 25 looks at breakdown of esculin. A positive test was recorded if the capule turns black and a negative test recorded if the capule remained purple. The biochemical profile obtained for Lr3613-1 was then analyzed and the species of the strain was identified using the APIweb identification software.

Results

Table 4 provides the API strip results for *Lactobacillus reuteri* 3613-1. As shown in Table 4, Lr3613-1 can utilize D-ribose, D-galactose, D-glucose, D-maltose, D-lactose, D-melibiose, sucrose, D-raffinose, and potassium gluconate as carbon sources.

TABLE 4

API strip results for Lr3613-1

| No | Carbohydrate of study | L. reuteri 3613-1 |
|---|---|---|
| 0 | Control | − |
| 1 | Glycerol | − |
| 2 | Erythritol | − |
| 3 | D-arabinose | − |
| 4 | L-arabinose | − |
| 5 | D-ribose | + |
| 6 | D-xylose | − |
| 7 | L-xylose | − |
| 8 | D-xylose | − |
| 9 | Methyl-beta-D-xylopyranoside | − |
| 10 | D-galactose | + |
| 11 | D-glucose | + |
| 12 | D-fructose | − |
| 13 | D-mannose | − |
| 14 | L-sorbose | − |
| 15 | L-rhamnose | − |
| 16 | Dulcitol | − |
| 17 | Inositol | − |
| 18 | D-mannitol | − |
| 19 | D-sorbitol | − |
| 20 | Methyl-alpha-D-mannopyranoside | − |
| 21 | Methyl-alpha-D-glucopyranoside | − |
| 22 | N-actylglucosamine | − |
| 23 | Amygdalin | − |
| 24 | Arbutin | − |
| 25 | Esculin ferric citrate | − |
| 26 | Salicin | − |
| 27 | D-cellobiose | − |
| 28 | D-maltose | + |
| 29 | D-lactose (bovine origin) | + |
| 30 | D-melibiose | + |
| 31 | D-saccharose (sucrose) | + |
| 32 | D-trehalose | − |
| 33 | Inulin | − |
| 34 | D-melezitose | − |
| 35 | D-raffinose | + |
| 36 | Amidon (starch) | − |
| 37 | Glycogen | − |
| 38 | Xylitol | − |
| 39 | Gentiobiose | − |
| 40 | D-turanose | − |
| 41 | D-lyxose | − |
| 42 | D-tagatose | − |
| 43 | D-fucose | − |
| 44 | L-fucose | − |
| 45 | D-arabitol | − |
| 46 | L-arabitol | − |
| 47 | Potassium gluconate | + |
| 48 | Potassium 2-ketogluconate | − |
| 49 | Potassium 5-ketogluconate | − |

The embodiments and examples are representative only and not intended to limit the scope of the claims.

The invention claimed is:

1. A method of reducing amount or growth of a pathogenic microbe of the urogenital tract, the method comprising administering to a subject or a sample a composition comprising an effective amount of *Lactobacillus reuteri* 3613 (Lr3613) deposited under NRRL accession number B-67262 and/or *Lactobacillus reuteri* 3613-1 (Lr3613-1) deposited under NRRL accession number B-68035,
    wherein the pathogenic microbe of the urogenital tract comprises one or more of *Escherichia coli*, *Gardnerella vaginalis*, and a *Candida* species, wherein the effective amount of *Lactobacillus reuteri* 3613, *Lactobacillus reuteri* 3613-1, or a combination thereof is from $1 \times 10^8$ CFU to $1 \times 10^{11}$ CFU per dose of administration, from $1 \times 10^6$ CFU/g to $1 \times 10^{10}$ CFU/g, or from $1 \times 10^6$ CFU/ml to $1 \times 10^{10}$ CFU/ml, and wherein the effective amount of Lr3613 and/or Lr3613-1 reduces the amount of growth of one or more of *Escherichia coli, Gardnerella vaginalis*, and a *Candida* species in the subject or the sample.

2. The method of claim 1, comprising administering the composition to a subject.

3. The method of claim 1, wherein the effective amount of *Lactobacillus reuteri* 3613, *Lactobacillus reuteri* 3613-1, or a combination thereof is from $1 \times 10^8$ CFU to $1 \times 10^{11}$ CFU per dose of administration.

4. The method of claim 1, wherein the effective amount of Lr3613, Lr3613-1, or a combination of Lr3613 and Lr3613-1 is from $1 \times 10^6$ CFU/g to $1 \times 10^{10}$ CFU/g or $1 \times 10^6$ CFU/ml to $1 \times 10^{10}$ CFU/ml.

5. The method of claim 1, wherein the composition comprises a lyophilized culture of Lr3613 and/or Lr3613-1, or a liquid culture of Lr3613 and/or Lr3613-1.

6. The method of claim 1, wherein the composition further comprises one or more of an adjuvant, a carrier, or an excipient, wherein the adjuvant, carrier, or excipient does not naturally occur with the Lr3613 and/or Lr3613-1 bacterial strain.

7. The method of claim 1, wherein the composition further comprises a prebiotic, glycerol, and/or juice.

8. The method of claim 1, wherein administering the composition reduces amount or growth of the pathogenic microbe by at least 80%.

9. The method of claim 2, wherein the amount or growth of the pathogenic microbe is reduced in a urogenital tract of the subject.

10. The method of claim 9, wherein administering the composition reduces amount or growth of the pathogenic microbe by at least 80% in the urogenital tract of the subject.

11. The method of claim 9, wherein at least one symptom, sign, or condition of urogenital tract infection is reduced or prevented in the subject.

12. The method of claim 11, wherein the at least one symptom, sign, or condition comprises one or more of pain or burning sensation while urinating or during intercourse; frequent urination; urge to urinate despite having an empty bladder; urine that is bloody, cloudy, or foul-smelling; pressure or cramping in groin, lower abdomen, or back; pain, irritation, or itching in urogenital area; redness, swelling, rash, or pain in vagina or vulva; vaginal discharge that is irregular, watery, thick, white, green, yellow, or foul-smelling; fever; chills; bacterial vaginosis; preterm delivery caused by bacterial vaginosis in pregnancy; *Lactobacillus* deficiency; chronic bacterial vaginosis; chronic yeast infection; chronic urogenital tract infection in menopause; atrophic vaginitis; atrophic vaginosis; and a vulva-vaginal candidiasis.

13. The method of claim 2, comprising administering the composition via oral administration, rectal administration, vaginal administration, urinary tract or urinary bladder administration, or a combination thereof.

14. The method of claim 2, comprising administering the composition in a form of a solution, a suspension, an emulsion, a suppository, a lubricant, a capsule, a coated capsule, a gel, a paste, a tablet, a buccal tablet, a powder, a sachet, a troch, a pill, a syrup, a thick syrup, a chewable gum, a pearl, a pessary, a vial, a topical preparation, or a combination thereof.

15. The method of claim 2, comprising administering the composition once daily.

16. The method of claim 2, comprising administering the composition for a period of 10 days to 120 days.

17. The method of claim 2, comprising administering a prebiotic or juice simultaneously or sequentially with the composition.

18. The method of claim 1, wherein administering the composition reduces amount or growth of *Escherichia coli* by at least 80% in the subject or the sample.

19. The method of claim 1, wherein administering the composition reduces amount or growth of *Gardnerella vaginalis* by at least 80% in the subject or the sample.

20. The method of claim 1, wherein administering the composition reduces amount or growth of a *Candida* species by at least 80% in the subject or the sample.

* * * * *